(12) United States Patent
Vaisvila et al.

(10) Patent No.: US 6,846,658 B1
(45) Date of Patent: Jan. 25, 2005

(54) METHOD FOR CLONING AND PRODUCING THE MSEL RESTRICTION ENDONUCLEASE

(75) Inventors: Romualdas Vaisvila, Rockport, MA (US); Richard D. Morgan, Middleton, MA (US); Rebecca B. Kucera, Hamilton, MA (US); Toby E. Claus, Beverly, MA (US); Elisabeth A. Raleigh, Somerville, MA (US)

(73) Assignee: New England Biolabs, Inc., Beverly, MA (US)

( * ) Notice: Subject to any disclaimer, the term of this patent is extended or adjusted under 35 U.S.C. 154(b) by 99 days.

(21) Appl. No.: 09/689,343

(22) Filed: Oct. 12, 2000

(51) Int. Cl.[7] ............................ C12P 21/00; C12N 1/21; C12N 15/70

(52) U.S. Cl. ..................... 435/183; 435/320.1; 435/243; 435/252.1; 435/252.3; 536/23.1; 536/23.2; 536/23.7

(58) Field of Search .............................. 435/183, 320.1, 435/243, 252.1, 252.3, 69.1; 536/23.1, 23.2, 23.7

(56) References Cited

U.S. PATENT DOCUMENTS

| | | | |
|---|---|---|---|
| 5,179,015 | A | 1/1993 | Wilson et al. |
| 5,200,333 | A | 4/1993 | Wilson |
| 5,262,318 | A | 11/1993 | Guthrie |
| 5,320,957 | A | 6/1994 | Brooks et al. |
| 5,492,823 | A | 2/1996 | Xu |
| 5,498,535 | A | 3/1996 | Fomenkov et al. |
| 6,025,179 | A | 2/2000 | Lunnen et al. |
| 6,048,731 | A | 4/2000 | Kong et al. |

FOREIGN PATENT DOCUMENTS

| WO | WO 99/11821 | 3/1999 |
|---|---|---|

OTHER PUBLICATIONS

Yuan, R. Ann. Rev. Biochem. 50:285–315 (1981).
Smith and Nathans, J. Mol. Biol. 81:419–423 (1973).
Roberts and Macelis, Nucleic Acids Res. 28:306–307 (2000).
Wilson and Murray, Annu. Rev. Genet. 25:585–627 (1991).
Raleigh and Wilson, Proc. Natl. Acad. Sci. USA 83:9070–9074 (1986).
Heitman and Model, J. Bacteriology 169:3243–3250 (1987).
Raleigh, et al., Genetics 122:279–296 (1989).
Waite–Rees, et al., J. Bacteriology, 173:5207–5219 (1991).
Kosykh, et al., Molec. Gen. Genet. 178:717–719 (1980).
Mann, et al., Gene, 3:97–112 (1978).
Walder, et al., Proc. Natl. Acad. Sci. 78:1503–1507 (1981).
Szomolanyi, et al., Gene 10:219–225 (1980).
Janulaitis, et al., Gene 20:197–204 (1982).
Kiss and Baldauf, Gene 21:111–119 (1983).
Walder, et al. J. Biol. Chem. 258:1235–1241 (1983).
Fomenkov, et al., Nucleic Acids Res. 22:2399–2403 (1994).
Janulaitis, et al., Nucleic Acids Res. 20:6051–6056 (1992).
Bougueleret, et al., Nucleic Acids Res. 12:3659–3676 (1984).
Gingeras and Brooks, Proc. Natl. Acad. Sci. USA 80:402–406 (1983).
Theriault and Roy, Gene 19:355–359 (1982).
Blumenthal, et al., J. Bacteriol. 164:501–509 (1985).
Lunnen, et al., Gene, 74:25–32 (1988).
Piekarowicz, et al., Nucleic Acids Res. 19:1831–1835 (1991).
Piekarowicz, et al. J. Bacteriology 173:150–155 (1991).
Morgan, Nucleic Acids Res. 16:3104 (1988).
Kong, et al., Nucleic Acids Res. 28:3216–3223 (2000).
Stoker, et al., Gene 18:335–341 (1982).
Shizuya, et al., Proc. Natl. Acad. Sci. USA 89:8794–8797 (1992).
Harayama, et al., Mol. Gen. Genet. 184:52–55 (1981).
Wohlfarth, et al., J. Gen. Microbiol. 134:433–440 (1988).
Matsudaira, J. Biol Chem. 262:10035–10038 (1987).
Looney, et al., Gene 80:193–208 (1989).
Kiss, et al., Nucleic Acids Res. 13:6403–6421 (1985).

*Primary Examiner*—David Guzo
(74) *Attorney, Agent, or Firm*—Harriet M. Strimpel; Gregory D. Williams

(57) ABSTRACT

A method for cloning restriction-modification system is provided whereby the target modification methylase is produced and confers full protection during all growth phases in which the cognate restriction enzyme is present. The method is employed in the cloning of the MseI restriction-modification system.

6 Claims, 15 Drawing Sheets

FIG. 4

MleIM

```
  1 ATGCCTATCTCGACCGTCTGGACGCCGGACGGAGACGACCTCATC   SEQ ID NO:1
    M  P  I  S  T  V  W  T  P  D  G  D  D  L  I     SEQ ID NO:2
 46 GTGGAGGCGGACAACCTCGATTTCATTCAAACGCTCCCCGACGCG
    V  E  A  D  N  L  D  F  I  Q  T  L  P  D  A
 91 AGCTTCCGAATGATCTACATCGATCCGCCGTTCAACACAGGGCGA
    S  F  R  M  I  Y  I  D  P  P  F  N  T  G  R
136 ACGCAGCGGCTTCAGTCGCTCAAGACGACCCGCTCGGTCACAGGG
    T  Q  R  L  Q  S  L  K  T  T  R  S  V  T  G
181 TCGCGAGTCGGCTTCAAAGGCCAGACGTACGACACGGTCAAGAGC
    S  R  V  G  F  K  G  Q  T  Y  D  T  V  K  S
226 ACTCTGCACTCGTATGACGACGCTTTCACCGACTATTGGTCGTTC
    T  L  H  S  Y  D  D  A  F  T  D  Y  W  S  F
271 CTCGAACCGCGTCTCCTGGAGGCTTGGCGGTTGCTCACCCCTGAC
    L  E  P  R  L  L  E  A  W  R  L  L  T  P  D
316 GGCGCGCTCTATCTTCATCTGGATTACCGCGAGGTTCACTACGCC
    G  A  L  Y  L  H  L  D  Y  R  E  V  H  Y  A
361 AAGGTCGTCCTCGACGCGATGTTCGGACGCGAAAGCTTCCTGAAC
    K  V  V  L  D  A  M  F  G  R  E  S  F  L  N
406 GAGCTGATCTGGGCGTACGACTACGGCGCGCGCTCGAAGAGCAAG
    E  L  I  W  A  Y  D  Y  G  A  R  S  K  S  K
451 TGGCCCACCAAGCACGACAACATCCTCGTGTATGTGAAGGACCCG
    W  P  T  K  H  D  N  I  L  V  Y  V  K  D  P
496 AACAACTACGTCTGGAACGGTCAGGATGTAGATCGCGAGCCCTAC
    N  N  Y  V  W  N  G  Q  D  V  D  R  E  P  Y
541 ATGGCGCCCGGGCTCGTTACACCCGAGAAGGTAGCGCTTGGCAAG
    M  A  P  G  L  V  T  P  E  K  V  A  L  G  K
586 CTGCCCACCGACGTCTGGTGGCACACAATCGTTCCGCCTGCGAGC
    L  P  T  D  V  W  W  H  T  I  V  P  P  A  S
631 AAAGAGCGCACCGGGTACGCGACACAGAAGCCGGTCGGCATCATC
    K  E  R  T  G  Y  A  T  Q  K  P  V  G  I  I
676 CGTCGCATGATTCAGGCGAGCAGCAATGAAGGCGACTGGGTTCTG
    R  R  M  I  Q  A  S  S  N  E  G  D  W  V  L
721 GATTTCTTCGCTGGTAGTGGGACGACCGGCGCCGCGGCCCCGCAG
    D  F  F  A  G  S  G  T  T  G  A  A  A  R  Q
766 CTCGGACGCCGTTTTGTGCTCGTAGACGTCAACCCAGAAGCAATC
    L  G  R  R  F  V  L  V  D  V  N  P  E  A  I
811 GCGGTAATGGCAAAACGGTTGGATGACGGGGCATTGGACACCAGC
    A  V  M  A  K  R  L  D  D  G  A  L  D  T  S
856 GTGACGATCGTGCAGACTCCCCAGAGTGACCCACGAACCGACGGA
    V  T  I  V  Q  T  P  Q  S  D  P  R  T  D  G
901 TGA 903
```

FIG. 5 esaDix4IM

```
   1 ATGCCTACACTGGATTGGCCCGGTAAACAGTTAAGCTTCCCACCA    SEQ ID NO:3
     M  P  T  L  D  W  P  G  K  Q  L  S  F  P  P    SEQ ID NO:4
  46 GCTACCTCCTTGCATCTGGAGAGTGTGGTCACTGAGGGAGCGGAG
     A  T  S  L  H  L  E  S  V  V  T  E  G  A  E
  91 TCACCGCCTAATCGTCTGATTTGGGCGGACAACCTGCCGCTAATG
     S  P  P  N  R  L  I  W  A  D  N  L  P  L  M
 136 GTAGATTTGTTGGCCGAATATGAAGGGAAAATCGATCTGATCTAC
     V  D  L  L  A  E  Y  E  G  K  I  D  L  I  Y
 181 GCCGATCCCCCTTTTTTTACGGATCGTACTTATGCGGCGCGAATT
     A  D  P  P  F  F  T  D  R  T  Y  A  A  R  I
 226 GGTCATGGGGAGGATTCGCGTCGTCCACAAACCTGGCAGCTTGCA
     G  H  G  E  D  S  R  R  P  Q  T  W  Q  L  A
 271 GAAGGATATACGGACGAGTGGAAGGATTTAGATGAATACCTGGAC
     E  G  Y  T  D  E  W  K  D  L  D  E  Y  L  D
 316 TTCCTTTATCCACGCCTGGTACTGATGTATCGACTGCTGGCACCA
     F  L  Y  P  R  L  V  L  M  Y  R  L  L  A  P
 361 CACGGAACGCTCTACTTGCACCTGGACTGGCACGCCAATGCCTAC
     H  G  T  L  Y  L  H  L  D  W  H  A  N  A  Y
 406 GTACGTGTACTGCTTGATGAGATCTTCGGGCGACAGCGGTTTCTC
     V  R  V  L  L  D  E  I  F  G  R  Q  R  F  L
 451 AACGAGATCGTCTGGATCTATCACGGCCCCTCAGCCATCCGACGC
     N  E  I  V  W  I  Y  H  G  P  S  A  I  R  R
 496 GCCTTCAAGCGCAAACATGATACCATCTTGGTTTATGTGAAAGGT
     A  F  K  R  K  H  D  T  I  L  V  Y  V  K  G
 541 GAAAACTATACATTCAATGCGGATGCGGTTCGTCAACCTTACCAT
     E  N  Y  T  F  N  A  D  A  V  R  Q  P  Y  H
 586 CCGAGCACNCATAAGACCTTCGCTTCCTCCCCGAAGGCCGGCTTT
     P  S  T  H  K  T  F  A  S  S  P  K  A  G  F
 631 GGTAAGGTGCCGGATCTGCAGCGCGGCAAAGTGCCCGAAGACTGG
     G  K  V  P  D  L  Q  R  G  K  V  P  E  D  W
 676 TGGTATTTTCCGGTCGTGGCCCGTCTACACCGAGAACGGAGCGGC
     W  Y  F  P  V  V  A  R  L  H  R  E  R  S  G
 721 TATCCGACTCAAAAGCCTCAAGCCTTGCTGGAGCGGATCCTGCTG
     Y  P  T  Q  K  P  Q  A  L  L  E  R  I  L  L
 766 GCCTCCTCGAACGCAGGCGATCTGGTGGCAGACTTCTTCTGCGGC
     A  S  S  N  A  G  D  L  V  A  D  F  F  C  G
 811 TCAGGGACAACCGCTGTGGTGGCAGCCCGTCTGGGACGGCGCTTC
     S  G  T  T  A  V  V  A  A  R  L  G  R  R  F
 856 CTGGTCAACGATGCAAGCTGGCGCGCCGTTCATGTGACACGCACA
     L  V  N  D  A  S  W  R  A  V  H  V  T  R  T
 901 CGCTTGCTACGCGAGGGAGTAAGTTTCACTTTTGAACGCCAGGAA
     R  L  L  R  E  G  V  S  F  T  F  E  R  Q  E
 946 ACTTTTACTCTACCTATCCAGCCACTTCCACCAGATTGGTTGATC
     T  F  T  L  P  I  Q  P  L  P  P  D  W  L  I
 991 ATCGCCGAGGAGCAGATTCGCCTCCAAGCACCCTTTCTCGTAGAT
     I  A  E  E  Q  I  R  L  Q  A  P  F  L  V  D
1036 TTTTGGGAAGTGGACGATCAATGGGATGGCAAAATCTTCCGCAGC
     F  W  E  V  D  D  Q  W  D  G  K  I  F  R  S
1081 CGTCATCAAGGCTTACGCTCCCGCCTTCAGGAGCAGGCGCCGCTC
     R  H  Q  G  L  R  S  R  L  Q  E  Q  A  P  L
1126 TCTCTACCATTGACCGGGAATGGACTGTTGTGTGTACGGGTAGTG
     S  L  P  L  T  G  N  G  L  L  C  V  R  V  V
1171 AGCCGTGAAGGGGAATACTATGAGTTCACAGGTCGAGCCGATAGC
     S  R  E  G  E  Y  Y  E  F  T  G  R  A  D  S
1216 CCTCACCCCGTATCGTTTTGA 1236
     P  H  P  V  S  F  *
```

FIG. 6

```
  1 ATGATCACGAACCTGATGGAAAACGATGTCATTGGCAAAATCTAC   SEQ ID NO:5
    M  I  T  N  L  M  E  N  D  V  I  G  K  I  Y   SEQ ID NO:6
 46 TTTGCCGACAACATGGAAGTCCTGCGAGGGCTTCCGGCGGCGTCC
    F  A  D  N  M  E  V  L  R  G  L  P  A  A  S
 91 GTGGACCTGATCTACATCGATCCTCCGTTCAACACCGGAAAGGTT
    V  D  L  I  Y  I  D  P  P  F  N  T  G  K  V
136 CAGGAGCGCACTCAGCTCAAAACGGTGCGCTCCGAGTGGGGCGAT
    Q  E  R  T  Q  L  K  T  V  R  S  E  W  G  D
181 CGCGTCGGATTCCAGGGCCGTCGCTACGAAAGCATCGTCGTGGGT
    R  V  G  F  Q  G  R  R  Y  E  S  I  V  V  G
226 AAGAAGCGCTTTACCGACTTCTTCGACGACTATCTGGCTTTCCTG
    K  K  R  F  T  D  F  F  D  D  Y  L  A  F  L
271 GAACCGCGCCTGGTCGAAGCCCATCGTGTTCTGGCGCCGCACGGG
    E  P  R  L  V  E  A  H  R  V  L  A  P  H  G
316 TGCCTCTACTTTCACGTCGACTACCGCGAGGTGCACTACTGTAAG
    C  L  Y  F  H  V  D  Y  R  E  V  H  Y  C  K
361 GTCCTTCTTGACGGCATCTTCGGTCGCGAGGCCTTTCTCAACGAG
    V  L  L  D  G  I  F  G  R  E  A  F  L  N  E
406 ATCATCTGGGCCTACGATTACGGCGGGCGTCCGAAGGACAGGTGG
    I  I  W  A  Y  D  Y  G  G  R  P  K  D  R  W
451 CCTCCTAAGCACGACAACATCCTGCTCTACGCCAAGACTCCCGGT
    P  P  K  H  D  N  I  L  L  Y  A  K  T  P  G
496 CGCCACGTGTTCAATGCGGACGAAATCGAGCGCATTCCCTACATG
    R  H  V  F  N  A  D  E  I  E  R  I  P  Y  M
541 GCTCCGGGCCTGGTTGGCCCCGAAAAGGCAGCCCGTGGAAAACTG
    A  P  G  L  V  G  P  E  K  A  A  R  G  K  L
586 CCAACCGACACGTGGTGGCATACGATCGTTCCGACCAGCGGCTCC
    P  T  D  T  W  W  H  T  I  V  P  T  S  G  S
631 GAGAAGACCGGGTATCCAACCCAGAAACCTTTAGGGATTCTCCGC
    E  K  T  G  Y  P  T  Q  K  P  L  G  I  L  R
676 CGTATTGTGCAGGCATCGTCTCATCCGGGGGCAGTCGTGCTCGAC
    R  I  V  Q  A  S  S  H  P  G  A  V  V  L  D
721 TTCTTCGCCGGCAGTGGGACAACAGGGGTAGCGGCTTTTGAGTTG
    F  F  A  G  S  G  T  T  G  V  A  A  F  E  L
766 GGCCGGCGTTTCATTCTGGTCGATAACCATCCGGAGGCCCTCCAG
    G  R  R  F  I  L  V  D  N  H  P  E  A  L  Q
811 GTGATGGCCAGGCGCTTCGACGGCATCGAGGGGATCGAATGGGTG
    V  M  A  R  R  F  D  G  I  E  G  I  E  W  V
856 GGCTTCGATCCGACACCGTACCAGAAGGGCGCAAAGCAGCGCCGC
    G  F  D  P  T  P  Y  Q  K  G  A  K  Q  R  R
901 TCCTGCCCGGCGCCCACCGGGTAA  924
    S  C  P  A  P  T  G  *
```

FIG. 7 mseIR

```
  1 GTGACCCACGAACCGACGGATGATCCCGATTTCATAGTGATGGCC   SEQ ID NO:7
      M  T  H  E  P  T  D  D  P  D  F  I  V  M  A   SEQ ID NO:8
 46 GCGAGCGCGGCGAACCTCGCTGATCGGTACGTAGCGAGTGAAGAC
      A  S  A  A  N  L  A  D  R  Y  V  A  S  E  D
 91 GACCCCTGGGTCGGCAGCCCGTTCGAGTGGATCCTTCGCGTTCCA
      D  P  W  V  G  S  P  F  E  W  I  L  R  V  P
136 TCCAGAACGAAGGGCGCGGTCGGTGAGCTGCTCGTGAGCGAATGG
      S  R  T  K  G  A  V  G  E  L  L  V  S  E  W
181 GCTAATGCCAAAGGCCTCCGTGTGAAGAGGTCGGGGTCCAGCGAT
      A  N  A  K  G  L  R  V  K  R  S  G  S  S  D
226 GCGGACCGCGTGATCAACGGGCATCGCATCGAGATCAAGATGTCG
      A  D  R  V  I  N  G  H  R  I  E  I  K  M  S
271 ACTTTGTGGAAGTCCGGCGGCTTCAAGTTTCAGCAGATCCGGGAT
      T  L  W  K  S  G  G  F  K  F  Q  Q  I  R  D
316 CAGGAGTACGACTTTTGCCTCTGCCTTGGGATCAGCCCGTTCGAA
      Q  E  Y  D  F  C  L  C  L  G  I  S  P  F  E
361 GTGCACGCGTGGCTGCTGCCCAAAGACCTATTGCTTGAGTACGTG
      V  H  A  W  L  L  P  K  D  L  L  E  Y  V
406 ATTGGTCACATGGGTCAGCACACCGGCGCGAGCGGGAGCGACACT
      I  G  H  M  G  Q  H  T  G  A  S  G  S  D  T
451 GCGTGGCTGGGGTTCCCAGCGGACGAGCCGTATGACTGGATGCGC
      A  W  L  G  F  P  A  D  E  P  Y  D  W  M  R
496 CCTTTCGGAGGTCGCTTAGGTCACGTCGAAGATCTCCTCCTCGCG
      P  F  G  G  R  L  G  H  V  E  D  L  L  L  A
541 GCCGGCCCCGGTCCCTACTGA 561
      A  G  P  G  P  Y
```

FIG. 9A

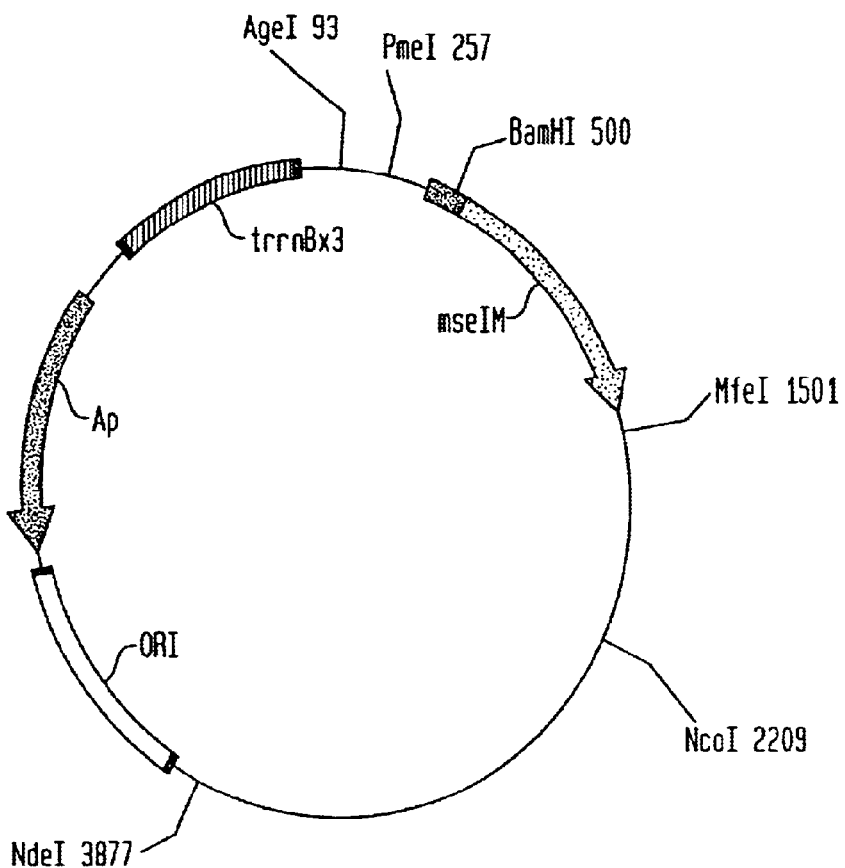

FIG. 9B

SEQ ID NO:9

AgeI
ACCGGTGATTGGACATTGCCGAAATCAGGCTGTCTCTCACTATTTGACGCACTGGCTG
GACTATCCACATCTACCTTATTCCCCCGAATAACGAGATCCCTTCCAGCACCGGGCAA
                             PmeI
TTGCCCGGTTTTTTTTGCGTTGAATTTGTCATTTTGTGCCGTGGTGTTTAAACCGCAC
    -35          -10
AGAATAAATTGTCGTGATTTCACCTTTAAAATAAAATTAAAAGAGAAAAAAATTCTCT
GTGGAAGGGCTATGTTAGATAAAATTGACCGTAAGCTGCTGGCCTTACTGCAGCAGGA
TTGCACCCTCTCTTTGCAGGCACTGGCTGAAGCCGTTAATCTGACAACCACCCCTTGC
TGGAAGCGCCTGAAACGGCTGGAGGACGACGGTATCCTTATCGGCAAAGTCGCCCTGC
 BamHI
TGGATCC

FIG. 14
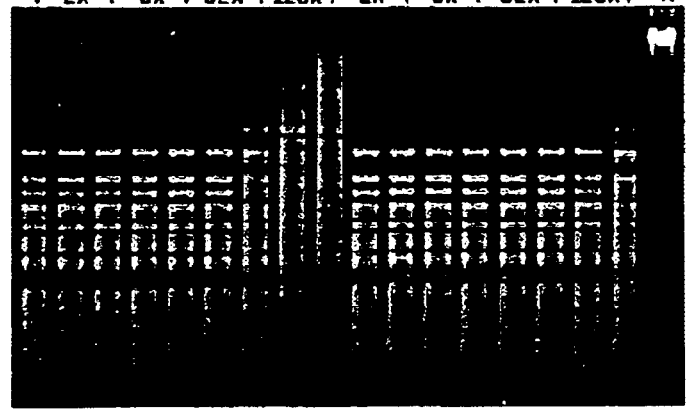
MseRM4
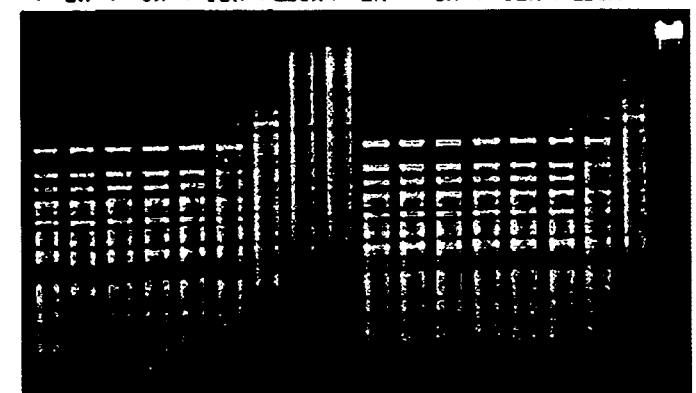
MseRM5
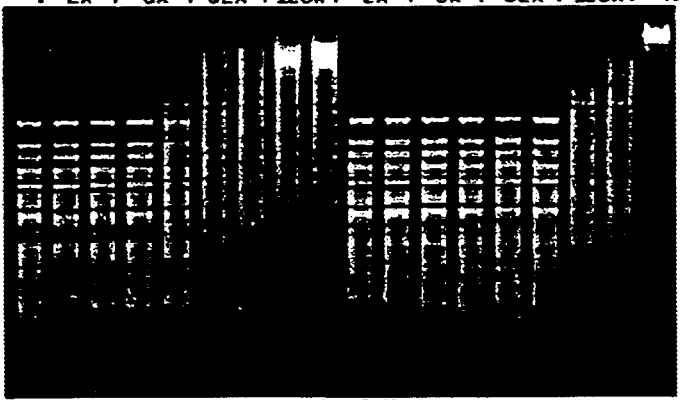
MseRM6

METHOD FOR CLONING AND PRODUCING THE MSEL RESTRICTION ENDONUCLEASE

BACKGROUND OF THE INVENTION

Restriction endonucleases belong to the class of enzymes called nucleases which degrade or cut single or double stranded DNA. A restriction endonuclease acts by recognizing and binding to particular sequences of nucleotides (the 'recognition sequence') along the DNA molecule. Once bound, the endonuclease cleaves the molecule within or to one side of the recognition sequence. The location of cleavage may differ among various restriction endonucleases, though for any given endonuclease the position is fixed. Different restriction endonucleases have different affinity for recognition sequences. More than two hundred restriction endonucleases recognizing unique specificities have been identified among thousands of bacterial and archaeal species that have been examined to date.

Restriction endonucleases are classified on the basis of their composition and cofactor requirements, the nature of target sequence, and the position of the site of DNA cleavage with respect to the target sequence (Yuan, R. Ann. Rev. Biochem., 50:285–315 (1981)). Currently three distinct, well-characterized classes of restriction endonucleases are known (I, II and III). Type I enzymes recognize specific sequences, but cleave randomly with respect to that sequence. The type III restriction endonucleases recognize specific sequences, cleave at a defined position to one side of that sequence, but never give complete digestion. Neither of these two kinds of enzymes is suitable for practical use. The type II restriction endonucleases recognize specific sequences (4–8 nucleotides long) and cleave at a defined position either within or very close to that sequence. Usually they require only $Mg^{2+}$ ions for their action. When they are purified away from other bacterial components, type II restriction endonucleases can be used in the laboratory to cleave DNA molecules into specific fragments. This property allows the researcher to manipulate the DNA molecule and analyze the resulting constructions.

Bacteria tend to possess at most, only a small number of restriction endonucleases per isolate. The restriction endonucleases are designated by a three-letter acronym derived from the name of organism in which they occur (Smith and Nathans, J. Mol. Biol. 81:419–423 (1973)). The first letter comes from the genus, and the second and third letters come from the species. Thus, a strain of the species *Deinococcus radiophilus* for example, synthesizes three different type II restriction endonucleases, named DraI, DraII and DraIII. These enzymes recognize and cleave the sequences TTTAAA, PuGGNCCPy and CACNNNGTG, respectively. *Escherichia coli* RY13, on the other hand, synthesizes only one type II restriction enzyme, EcOR1, which recognizes the sequence GAATTC (Roberts R. J and Macelis D., *Nucl. Acids Res.*, 28:306–7 (2000)).

A second component of bacterial and archaeal restriction systems are the modification methylases (Roberts and Halford, in 'Nucleases', $2^{nd}$ ed.'s, Linn et al., ed.'s, p. 35–88 (1993)). These enzymes are complementary to restriction endonucleases and they provide the means by which bacteria are able to protect their own DNA and distinguish it from foreign, invading DNA. Modification methylases recognize and bind to the same recognition sequence as the corresponding restriction endonuclease, but instead of cleaving the DNA, they chemically modify one or other of the nucleotides within the sequence by the addition of a methyl group. Following methylation, the recognition sequence is no longer cleaved by the restriction endonuclease. The DNA of a bacterial cell is modified by virtue of the activity of its modification methylase, and is therefore insensitive to the presence of the endogenous restriction endonuclease. It is only unmodified, and therefore identifiably foreign DNA, that is sensitive to restriction endonuclease recognition and cleavage.

It is thought that in nature, type II restriction endonucleases cleave foreign DNA such as viral and plasmid DNA when this DNA has not been modified by the appropriate modification enzyme (Wilson and Murray, *Annu. Rev. Genet.* 25:585–627 (1991)). In this way, cells are protected from invasion by foreign DNA. Thus, it has been widely believed that evolution of type II restriction modification systems has been driven by the cell's need to protect itself from infection by foreign DNA (the cellular defense hypothesis).

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within gene libraries. One potential difficulty is that some restriction endonuclease and methylase genes may not express in *E. coli* due to differences in the transcriptional and translational machinery of the source organism and of *E. coli*, such as differences in promotor or ribosome binding sites or the codon composition of the gene. The isolation of the methylase gene requires that the methylase express well enough in *E. coli* to fully protect at least some of the plasmids carrying the gene. The isolation of the endonuclease in active form requires that the methylase express well enough to protect the host DNA fully, or at least enough to prevent lethal damage from cleavage by the endonuclease. Another obstacle to cloning restriction-modification systems lies in the discovery that some strains of *E. coli* react adversely to cytosine or adenine modification; they possess systems that destroy DNA containing methylated cytosine (Raleigh and Wilson, *Proc. Natl. Acad. Sci., USA* 83:9070–9074, (1986)), or methylated adenine (Heitman and Model, J. Bact. 196:3243–3250, (1987)); Raleigh, et al., *Genetics*, 122:279–296, (1989)) Waite-Rees, et al., *J. Bacteriology*, 173:5207–5219 (1991)). Cytosine-specific or adenine-specific methylase genes cannot be cloned easily into these strains, either on their own, or together with their corresponding endonuclease genes. To avoid this problem it is necessary to use mutant strains of *E. coli* (McrA⁻and McrB⁻or Mrr⁻) in which these systems are defective.

Several approaches have been used to clone restriction genes into *E. coliL*

1) Selection Based on Phage Restriction

The first cloned systems used bacteriophage infection as a means of identifying or selecting restriction endonuclease clones (EcoRII: Kosykh et al., *Molec. Gen. Genet* 178:717–719, (1980)); HhaII: Mann et al., *Gene* 3:97–112, (1978)); PstI: Walder et al., *Proc. Nat Acad. Sci.* 78:1503–1507, (1981)). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival under standard conditions.

2) Selection Based on Vector Modification

A second approach which is being used to clone a growing number of systems, involves selection for an active methylase gene (refer to U.S. Pat. No. 5,200,333 and BsuRI: Kiss et al., *Nucl. Acid. Res.* 13:6403–6421, (1985)). Since restriction and modification genes are often closely linked, both genes can often be cloned simultaneously. This selection does not always yield a complete restriction system however, but instead may yield only the methyltransferase gene (BspRI: Szomolanyi et al., *Gene* 10:219–225, (1980); BcnI: Janulaitis et al, *Gene* 20:197–204 (1982); BsuRI: Kiss and Baldauf, *Gene* 21:111–119, (1983); and MspI: Walder et al., *J. Biol. Chem.* 258:1235–1241, (1983)).

3) Sub-cloning of Natural Plasmids

Another cloning approach involves transferring systems initially characterized as plasmid-borne into *E. coli* cloning plasmids (EcoRVI: Bougueleret et al., *Nucl. Acid. Res.* 12: 3659–3676, (1984); PaeR7I: Gingeras and Brooks, *Proc. Natl. Acad. Sci. USA* 80:402–406, (1983); Theriault and Roy, Gene 19:355–359 (1982); PvuII: Blumenthal et al., *J. Bacteriol.* 164:501–509, (1985)).

4) Multi-step Cloning

Sometimes the straight-forward methylase selection method fails to yield a methylase (and/or endonuclease) clone due to various obstacles. See, e.g., Lunnen, et at., *Gene*, 74(1):25–32 (1988). One potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease (see, U.S. Pat. No. 5,320, 957).

5) Selection Based on Induction of the DNA-damage-inducible SOS Response

Another method for cloning methylase and endonuclease genes is based on a colorimetric assay for DNA damage (see, U.S. Pat. No. 5,492,823). When screening for a methylase, the plasmid library is transformed into a sensitive host *E. coli* strain such as AP1-200. The expression of a methylase will induce the SOS response in an *E. coli* strain which is McrA$^+$, McrBC$^+$, or Mrr$^+$. The AP1-200 strain is temperature sensitive for the Mcr and Mrr systems and includes a lacZ gene fused to the damage inducible dinD locus of *E. coli*. The detection of recombinant plasmids encoding a methylase or endonuclease gene is based on induction at the restrictive temperature of the lacZ gene. Transformants encoding methylase genes are detected on LB agar plates containing X-gal as blue colonies. (Piekarowicz, et.al., *Nucleic Acids Res.* 19:1831–1835, (1991) and Piekarowicz, et.al. J. Bacteriology 173:150–155 (1991)). Likewise, the *E. coli* strain ER1992 contains a dinD1-Lac Z fusion but is lacking the methylation dependent restriction systems McrA, McrBC and Mrr. In this system (called the "endo-blue" method), the endonuclease gene can be detected in the absence of it's cognate methylase when the endonuclease damages the host cell DNA, inducing the SOS response. The SOS-induced cells form deep blue colonies on LB agar plates supplemented with X-gal. (Fomenkov, et.al. *Nucleic Acids Res.* 22:2399–2403 (1994) and U.S. Pat. No. 5,498, 535).

6) N-terminal-sequence-based Degenerate Inverse PCR Method

It may occur that a modification methyltransferase gene cannot be identified (see, U.S. Pat. No. 5,945,288), or that a methylase gene can be identified but the open reading frame specifying the restriction endonuclease is uncertain. In these cases, an additional procedure for identifying the gene for the endonuclease specifically can be applied when the restriction endonuclease can be purified in sufficient quantity and purity from the original organism. In this method, the restriction endonuclease is purified to substantial homogeneity and subjected to polypeptide sequencing. The polypeptide sequence obtained is reverse-translated into DNA sequence and degenerate PCR primers can be designed to amplify a portion of the endonuclease gene from genomic DNA of the original organism or from a gene library made therefrom. The DNA sequence of the complete genes can be obtained by methods dependent on Southern blot analysis or by further direct or inverse PCR methods. If the cognate methyltransferase gene cannot be obtained or cannot be expressed, the stability and utility of the solo restriction endonuclease clone will usually be severely compromised.

It may occur that genes for both the methyltransferase and the restriction endonuclease of a particular system can be obtained by the methods described above, but nevertheless establishment of a usable strain for enzyme production is problematic. Frequently the difficulty is with expression of the methyltransferase gene at a suitable level. This is particularly true with method (6). Such clones sometimes can be stabilized by using heterospecific methyltransferase genes, which were not associated with the endonuclease gene in the original host but which recognize the same or a related sequence and prevent the endonuclease from cleaving its recognition sequence (see, U.S. Pat. No. 6,048,731).

It may occur that there is no suitable heterospecific methyltransferase available, and the degree of protection conferred on the host by the cognate methyltransferase is inadequate; or it may occur that apparently adequate levels of methyltransferase can be obtained but such level is toxic to the cell, resulting in strains that cannot be stored; or it may occur that protection is apparently adequate and the protected strain is viable, but the combination of the methyltransferase and the endonuclease genes gives a strain that does not express detectable endonuclease; or it may occur that protection is apparently adequate, but the combination of the methyltransferase and the endonuclease genes gives a strain that expresses detectable endonuclease, but is not sufficiently stable to make commercially useful levels of enzyme.

Many factors can be imagined that might alter the requisite level of enzyme needed for effective protection of the host cell from cleavage by a restriction endonuclease. Such factors include rapid growth, during which more DNA copies are present in the cell than are present during the stationary phase of growth; recovery from a resting state, during which time new synthesis of the modification methyltransferase may be required before new synthesis of the restriction endonuclease begins; starvation of various sorts, during which time levels of required DNA methyltransferase cofactors such as S-adenosylmethionine may be altered; and special physiological states, such as DNA damage or other physiological insults. In addition, levels of methyltransferase can potentially be too high and become toxic, for example by binding to or methylating extraneous sites related to the cognate site and thus interfering with the reading of the DNA sequence by regulatory or DNA-condensing proteins. Thus, the absolute level of expression of the methyltransferase may need to fluctuate in response to conditions over the life of a culture, in order to be indefinitely perpetuated.

This need for a fine level of control is not unique to modification methyltransferases. Over the course of 50 years of study, many detailed regulatory schemes have been described for various sorts of functions, such as catabolic and anabolic gene sets that break down nutrients (lac, ara, gal) or synthesize essential compounds (trp, his), or response to stressors (the DNA damage response, the heat shock response). These regulatory effects are mediated by changes in promoter activity (by activators or repressors), in transcript stability (by retroregulatory elements), by alteration of translation levels (by attenuation or translational coupling), for example. Despite this high level of understanding, it is not straighforward to anticipate in advance how the demand for a function will change with physiological changes and how to achieve the desired level of a function.

Because purified restriction endonucleases, and to a lesser extent, modification methylases, are useful tools for characterizing genes in the laboratory, there is a commercial incentive to obtain bacterial strains through recombinant DNA techniques that synthesize these enzymes in abundance. Such strains would be useful because they would simplify the task of purification as well as providing the means for production in commercially useful amounts.

SUMMARY OF THE INVENTION

In one embodiment, the present invention relates to a method for cloning and expressing a target restriction modification system, comprising first implementing a method for producing a balanced level of activity of a protective modification methyltransferase, such that expression compensates for changes in the physiological state of the cell and therefore confers full protection preferably during all growth phases from cleavage by the cognate restriction endonuclease; and then introducing the restriction endonuclease gene and providing for its expression.

The invention further relates to the method for producing a balanced level of activity of a protective modification methyltransferase comprising specifically testing for the extent of protection during critical growth phases which may be selected from stationary phase, the logarithmic phase of growth, recovery from storage or other growth phases, and then identifying a suitable expression vector by selecting for its function at those critical growth phases.

The above method is exemplified by the cloning and expression of the MseI restriction modification system, which is encoded on a DNA (deoxyribonucleic acid) fragment, which fragment codes for two related enzymes, namely an enzyme which recognizes the DNA sequence 5'-TTAA-3' and cleaves the phosphodiester bond between the T residues of this recognition sequence to produce a 2 base 5' extension (Morgan R. D., *Nucl. Acids Res.*, 16:3104 (1988)) (hereinafter referred to as the MseI restriction endonuclease), and a second enzyme, known as M.MseI, that recognizes the same DNA sequence, 5'-TTAA-3', but modifies this sequence by the addition of a methyl group to prevent cleavage by the MseI endonuclease. In addition, the invention relates to two additional DNA fragments, each of which encodes an enzyme differing in sequence from M.MseI that perform the same function as M.MseI, namely modifying the sequence 5'-TTAA-3' by the addition of a methyl group thus preventing cleavage by the MseI endonuclease. The present invention also relates to a process for preparing the DNA fragment, a vector containing the DNA fragment, a transformed host containing this DNA fragment, and an improved process for producing MseI restriction endonuclease from such a transformed host.

MseI restriction endonuclease produced according to the present invention is substantially pure and free of the contaminants commonly found in restriction endonuclease preparations made by conventional techniques.

The MseI methylase gene, but not the MseI endonuclease gene, was obtained generally in accordance with the technique referred to as methylase selection (U.S. Pat. No. 5,200,333, the disclosure of which is hereby incorporated by reference herein). However none of the clones obtained by methylase selection expressed detectable MseI restriction endonuclease activity and none was fully protected from MseI digestion after overnight incubation. A methylase clone was sequenced and the MseI methylase gene was identified based on homology to other N6-adenine methylases. Although the methylase clone did not produce any detectable MseI endonuclease activity, it was speculated that the endonuclease gene was likely located adjacent to the methylase gene. DNA contiguous to the MseI methylase gene was therefore amplified from *Micrococcus* species by inverse PCR techniques and sequenced.

To locate and positively identify the mseI endonuclease gene, the N-terminal amino acid sequence of highly purified mseI restriction endonuclease protein obtained from *Micrococcus* species was determined. An open reading frame in which the deduced amino acid sequence matched the N-terminal amino acid sequence of the MseI endonuclease was observed in the DNA sequence obtained by inverse PCR techniques and located 3' of the methylase gene. The MseI methylase gene was amplified and cloned into a vector compatible with a standard high expression vector. The MseI endonuclease gene was then amplified, ligated to an expression vector such as the pET series of vectors, and introduced into a host which was pre-modified with the MseI methylase carried on a separate compatible vector; however, no MseI activity was found in the few such constructs obtained. From further results below, it appears that this failure of MseI expression from inadequate expression of the methylase so that successful endonuclease expression became a lethal event. After obtaining a fully modifying vector in accordance with the present invention, the expression of the endonuclease was also carefully regulated by construction of a vector which suppressed expression of the endonuclease during cell growth prior to the induction of the endonuclease gene. A host carrying the endonuclease and methylase genes in these special constructs was then grown, induced and harvested and used to make the MseI endonuclease.

The preferred method for cloning and expressing the MseI restriction-modification system consists of obtaining methylase positive clones according to methylase selection method and determining the DNA sequence of these MseI methylase positive clones. The DNA adjacent to the methylase gene is obtained by inverse PCR techniques and sequenced. The MseI endonuclease protein from *Micrococcus* species is purified to near homogeneity and the N-terminal amino acid sequence determined. The MseI endonuclease gene is identified based on the DNA sequence and amino acid sequence data. The expression of the MseI methylase is modulated to achieve full protection of the host genome without creating so much methylase expression as to be toxic to the host. This full methylation state is monitored by testing DNA obtained from cells in rapid logarithmic growth for protection from MseI endonuclease cleavage and using a construct which provides full protection under these rapid growth conditions. The MseI endonuclease is then expressed by amplifying the complete gene from *Micrococcus* species genomic DNA and ligating it into an expression vector designed to limit expression of the MseI endonuclease during cell growth prior to induction, such as pVR-24 (New England Biolabs, Inc., Beverly, Mass.). The construct is introduced into a host with appropriate genetic composition to provide sufficient regulatory capacity (U.S. application Ser. No. 09/689,359, now U.S. Pat. No. 6,569,669 which is premodified at MseI sites by virtue of carrying the MseI methylase gene expressed on the separate compatible plasmid providing full protection against MseI cleavage. The MseI endonuclease is produced by growing the host containing the MseI endonuclease and methylase genes, inducing with the appropriate expression conditions, harvesting the cells and purifying the MseI endonuclease therefrom.

BRIEF DESCRIPTION OF THE DRAWINGS

FIG. 4 shows the DNA sequence of mseIM gene (SEQ ID NO: 1) and its encoded amino acid sequence (SEQ ID NO: 2).

FIG. 5 shows the DNA sequence of esaDix4IM gene (SEQ ID NO:3) and its encoded amino acid sequence (SEQ ID NO:4).

FIG. 6 shows the DNA sequence of esaDix5IM gene (SEQ ID NO:5) and its encoded amino acid sequence (SEQ ID NO:6).

FIG. 7 shows the DNA sequence of mseIR gene (SEQ ID NO:7) and its encoded amino acid sequence (SEQ ID NO:8).

FIG. 9A shows a restriction map of the recombinant plasmid pNKR1707 mseIM-9 encoding the MseI DNA methyltransferase gene and upstream regulatory elements.

FIG. 9B shows the DNA sequence upstream of MseI DNA methyltransferase gene (SEQ ID NO:9) which contains an optimal promoter sequence.

FIG. 14 shows an assay of MseI restriction endonuclease activity in crude cell extracts made from E. coli strains MseRM4, MseRM5 and MseRM6. The growth conditions are described in Example IV.

DETAILED DESCRIPTION OF THE INVENTION

Figure 1:
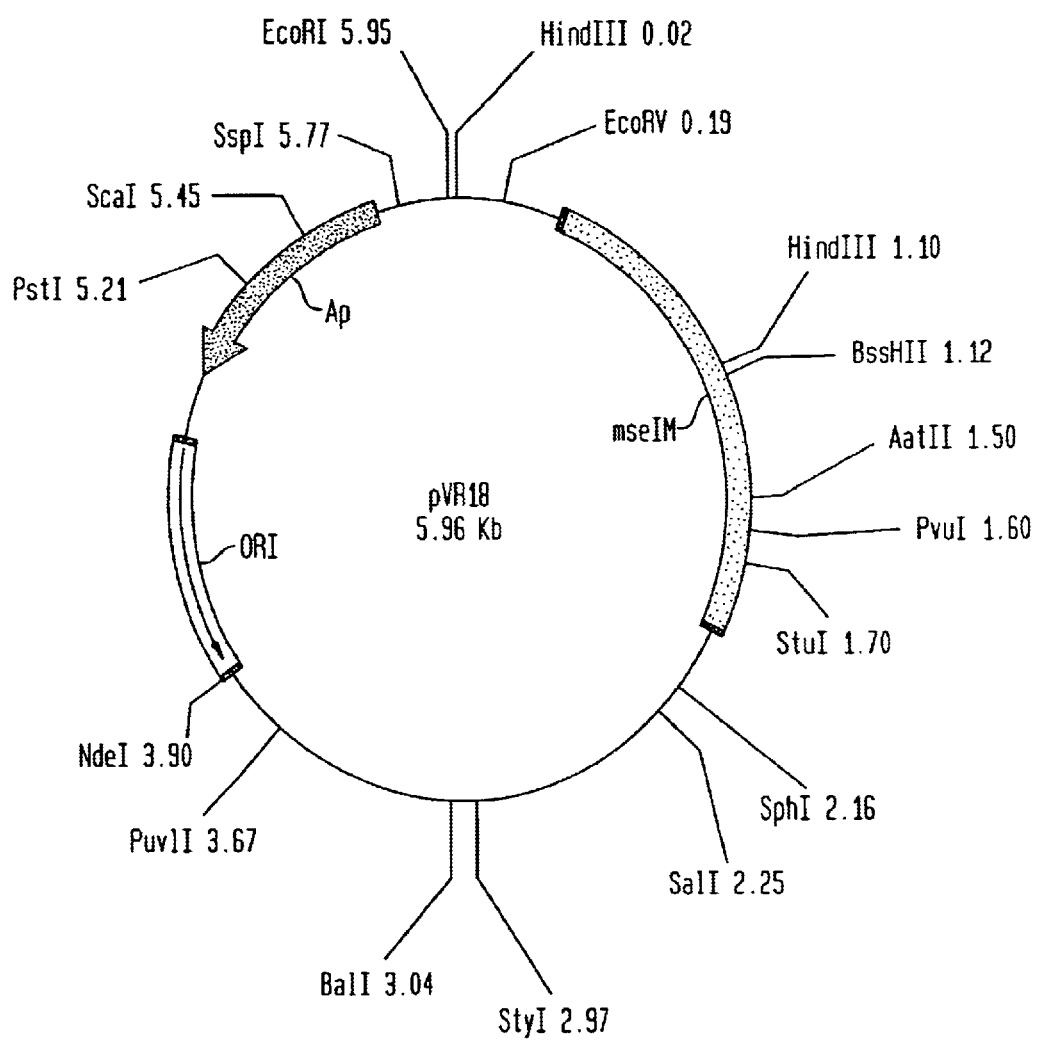
FIG. 1A shows a restriction map of the recombinant plasmid pVR-18 encoding MseI DNA methyltransferase gene.
Figure 2A:
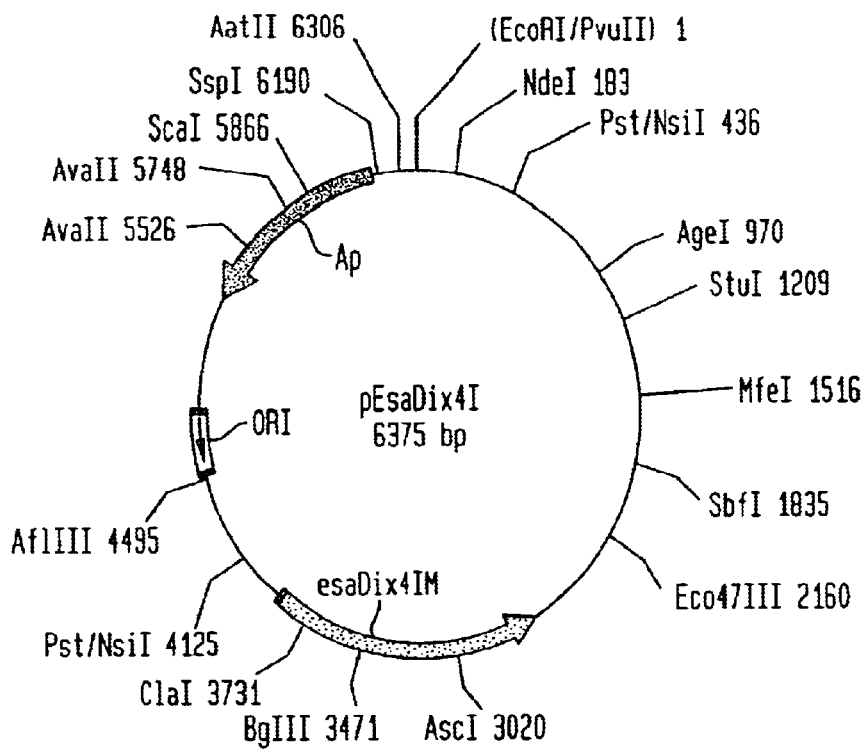
FIG. 2A shows a restriction map of the recombinant plasmid pEsaDix4I encoding putative DNA methyltransferase gene.
Figure 3A:
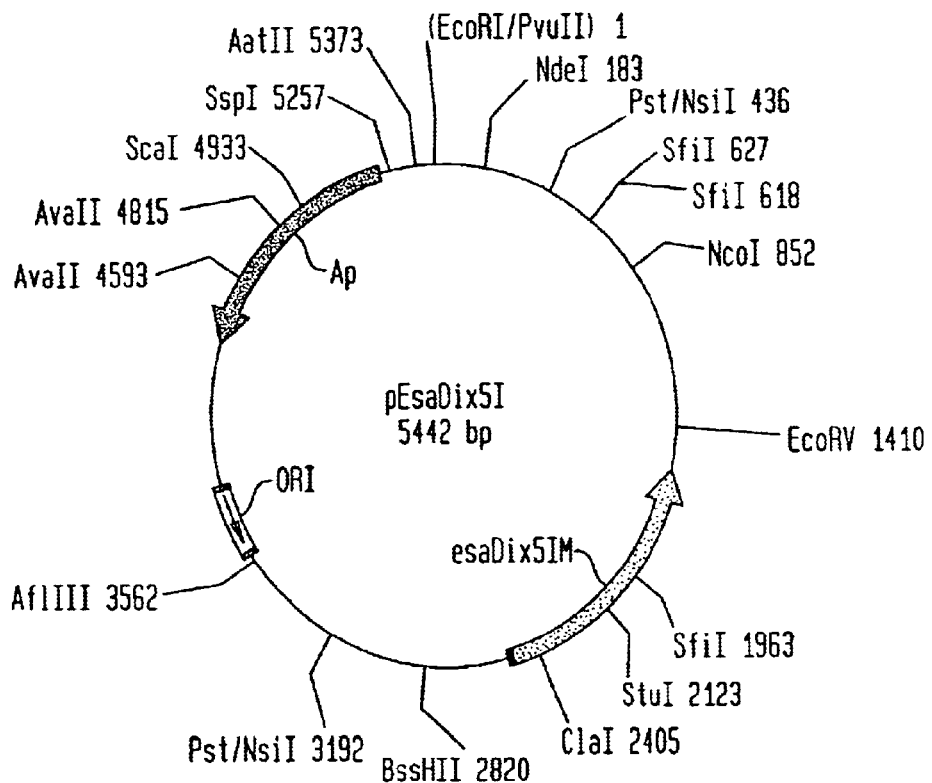
FIG. 3A shows a restriction map of the recombinant plasmid pEsaDix5I encoding putative DNA methyltransferase gene.
Figure 2B:
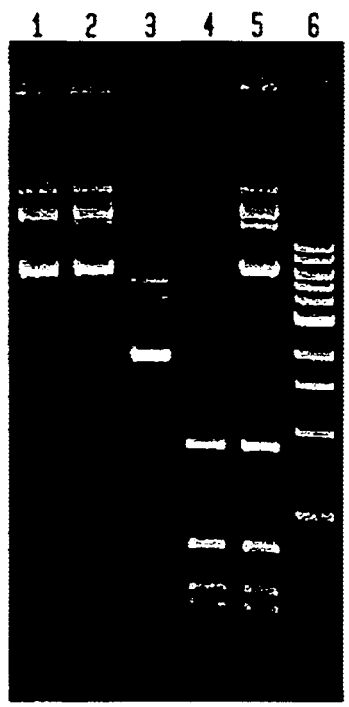
FIG. 2B shows the agarose gel analysis of the susceptibility to MseI of pEsaDix4I plasmid encoding a putative DNA methyltransferase gene. Lane 1, uncut pEsaDix4I; lane 2, pEsaDix4I following overnight incubation with ten units of MseI; lane 3, uncut pUC19; lane 4, pUC19 following overnight incubation with ten units of MseI; lane 4, pEsaDix4I+pUC19 following overnight incubation with ten units of MseI; lane 5, molecular weight standard (1 kb DNA Ladder, New England Biolabs, Inc.).
Figure 3B:
FIG. 3B shows the agarose gel analysis of the susceptibility to MseI of pEsaDix5I plasmid encoding putative DNA methyltransferase gene. Lane 1, uncut pEsaDlx5I; lane 2, pEsaDix5I following overnight incubation with ten units of MseI; lane 3, uncut pUC19; lane 4, pUC19 following overnight incubation with ten units of MseI; lane 4, pEsaDix5I+pUC19 following overnight incubation with ten units of MseI; lane 5, molecular weight standard (1 kb DNA Ladder, New England Biolabs, Inc.).
Figure 8:
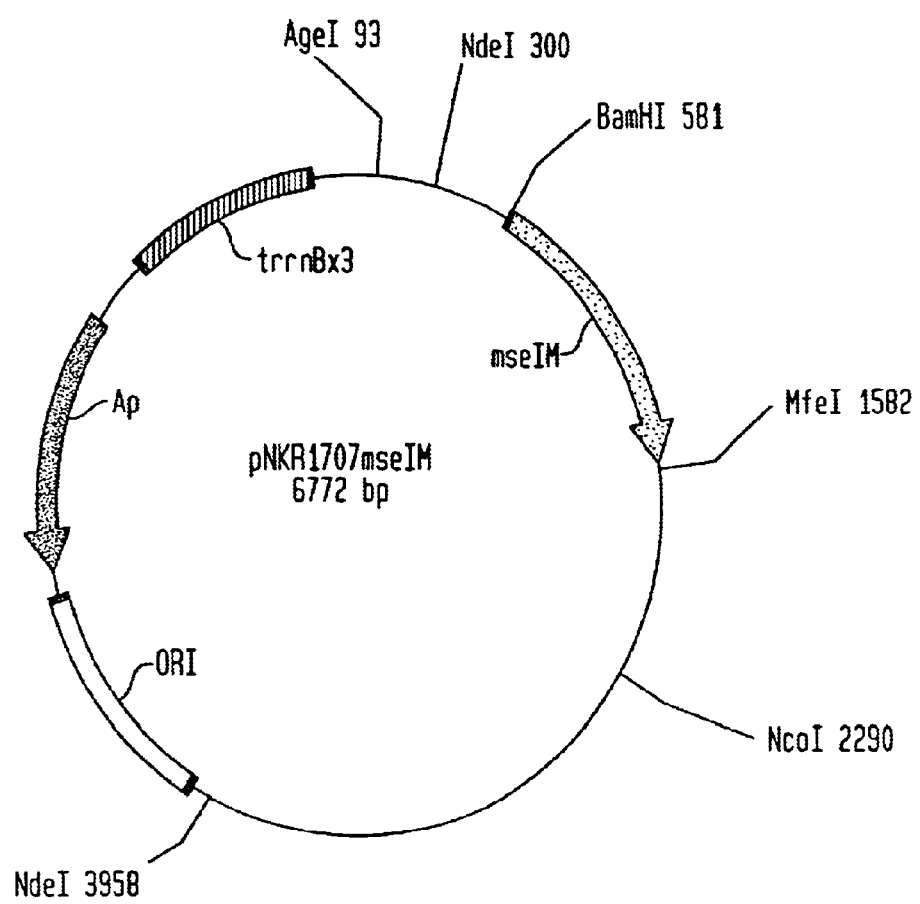
FIG. 8 shows a restriction map of the recombinant plasmid pNKR1707 mseIM used for construction of a library of constitutive promoters randoming mutagenized by error-prone PCR.
Figure 10:
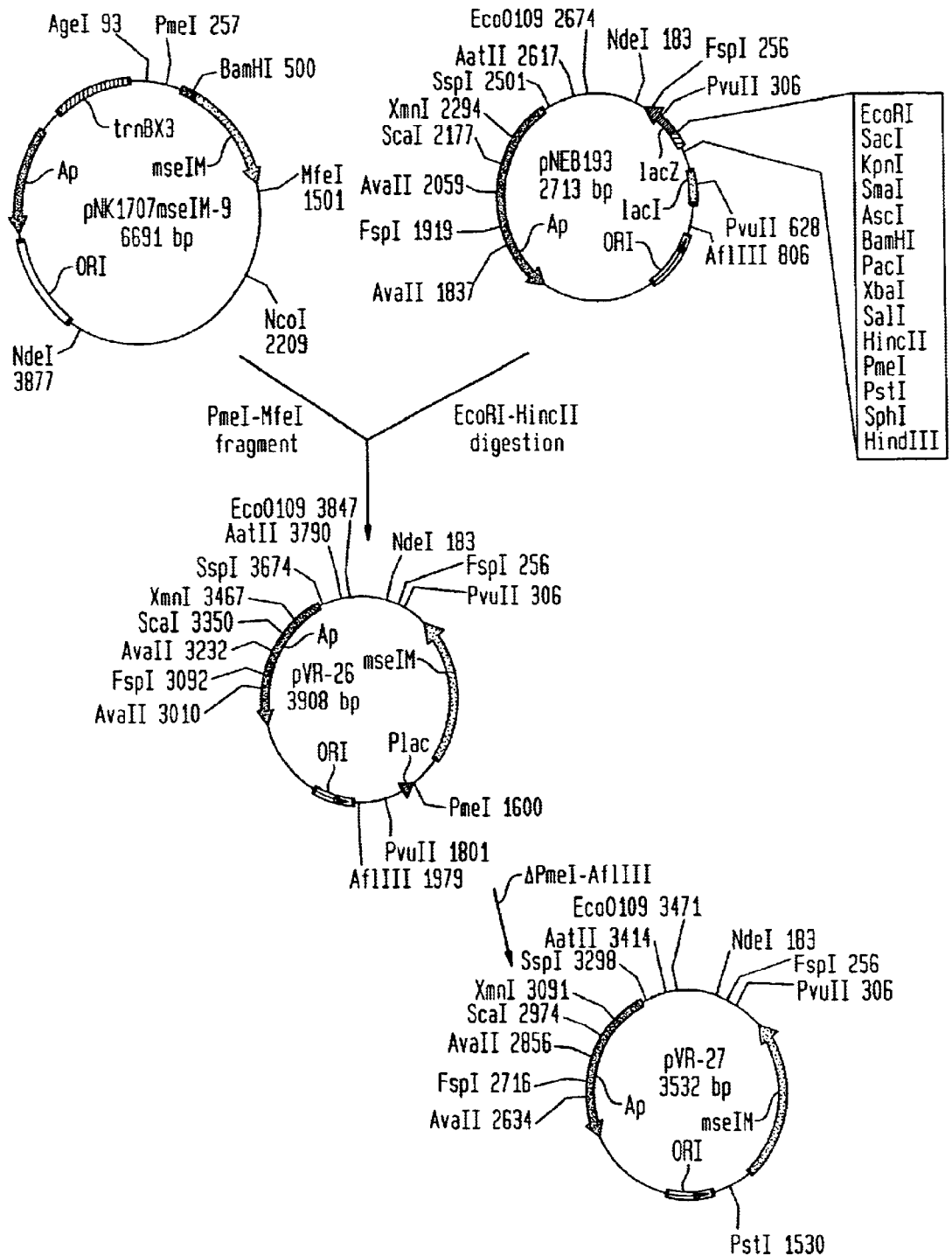
FIG. 10 shows the construction of the plasmids pVR-26 and pVR-27 used for controlled expression of MseI DNA methyltransferase gene.

In one embodiment, the present invention relates to a method of producing a target restriction endonuclease by first providing a vector expressing a modification methyltransferase gene protecting DNA from restriction enzyme cleavage, in such a form that complete protection of the host DNA is observed preferably at all growth phases in which the cognate restriction endonuclease is present without leading to toxicity (a fully-protecting methyltransferase vector), followed by providing a vector expressing the desired restriction endonuclease gene. The present invention is not limited by the identity of the modification methyltransferase gene or restriction enzyme, except that the modification methyltransferase must protect against cleavage by the said restriction enzyme.

In a preferred embodiment, the fully-protecting methyltransferase vector may be obtained by identifying regulatory elements capable of driving methyltransferase expression to provide full protection during a phase of growth that is especially sensitive to methyltransferase expression pattern. In accordance with the present invention, this may be done by the following steps:

(1) obtaining a methyltransferase gene in a vector by methods known in the art;

(2) placing a regulatory element such as a promoter in a suitable location with respect to the gene;

(3) transformation into the desired host cell;

(4) reisolation of vector from the pooled transformants during the time that they are in the logarithmic phase of growth;

(5) selection by digestion with the endonuclease; and (6) retransformation of the surviving undigested and thus protected vector population into a fresh host.

It will be understood by those skilled in the art that step (4) of this procedure may be performed with pooled vector isolated from logarithmic phase or from various other phases of growth, for example from stationary phase, from a resting state achieved by starvation for carbon or nitrogen or other essential nutrient, or from cells in a special physiological state, such as a state of DNA damage, or in the presence of physiological insults such as acidic media or toxic compounds, as may be appropriate.

In a preferred embodiment, the regulatory element of step (2) is identified by a procedure comprising the following steps:

(a) cloning into the vector containing the methyltransferase gene, at a desired location, a pool of fragments containing various distinct regulatory elements; and (b) proceeding with steps (3) through (6).

It will further be understood by those skilled in the art that the process of selection comprising steps (3) through (6) may be repeated to select further improvement.

It will further be understood by those skilled in the art that step (2a), cloning a pool of fragments containing regulatory elements at the same or a different location, may be repeated followed by repeated selection as may be appropriate.

The present invention is not limited by the identity of the regulatory element, which may be a promoter, an operator, an enhancer, or a down-stream regulatory element.

In a preferred embodiment, the methyltransferase gene of step (1) is isolated by the methylase selection procedure (U.S. Pat. No. 5,200,333). The present invention is not limited to methyltransferase genes isolated in this way but includes genes isolated by any of the methods described above such as phage selection, subcloning of natural plasmids, identification based on induction of the DNA-damage-inducible SOS response, by inverse PCR based on amino acid sequence of a purified protein, or identification in sequence databases from similarity to sequences of other methyltransferase followed by cloning by PCR or by Southern blot based procedures (see e.g., Kong, et al., *Nucleic Acids Res.* 28:3216–3223 (2000)).

In a preferred embodiment, the collection of distinct regulatory elements of step (2a) comprises copies of the his promoter of *S. typhimurium* randomly mutagenized by error-prone PCR together with such contaminating chromosomal fragments as may be present in the preparation of mutagenized fragments. The present invention is not limited to fragments obtained in this way, but may include collections of fragments isolated from genomic DNA of *E. coli* or another organism or fragments derived by oligonucleotide synthesis with degenerate sequences at random or specific locations or fragments derived by recombinational PCR of a random or specific collection of fragments. In a preferred embodiment, the regulatory element obtained in this way is the sequence of SEQ ID NO:9.

It will further be understood by one skilled in the art that this method may be applied to any methyltransferase that confers protection from cleavage by the restriction endonuclease in question, not merely that which co-occurs with the said endonuclease in a particular natural isolate.

The present invention further relates to the isolation of methyltransferase genes of desired specificity from DNA of environmental sources without first culturing the organisms contained therein. In a preferred embodiment, these genes are isolated by methylase selection from DNA made from a sample of a mixed green filament and mat community of prokaryotes growing at 68° C. at Dixie Valley Hot Spring, Nev.

The present invention further relates to provision of a desired restriction endonuclease gene expressed from a vector with tight regulation such that extremely low levels of protein are expressed in the absence of induction (very low basal expression is observed). In a preferred embodiment this tight regulation vector comprises a vector with antagonistic and independently regulatable promoters reading through the cloned target gene as described in WO 99/11821 and U.S. application Ser. No. 09/486,356(now U.S. Pat. No. 6,383,770) but basal expression has been further lowered by providing for a lower copy number than is present in the previously existing vector pLT7K used for this purpose. In a preferred embodiment, the copy number of the vector is lowered by exchanging the replication origin of pLT7K for that of pACYC184. Other replication origins might also be used, such as those of pSC101 (Stoker, et al., *Gene* 18:335–341 (1982)), pSYX20 (U.S. Pat. No. 5,262,318), F (Shizuya, et al., *Proc. Natl. Acad. Sci. USA* 89(18) :8794–8797 (1992)) or other low-copy vectors (Harayama, et al., *Mol. Gen. Genet.* 184:52–55 (1981) and Wohlfarth, et al., *J. Gen. Microbiol.* 134:433–440 (1988)). In a preferred embodiment, the vector is pVR-24.

In a preferred embodiment, further lowering of basal expression level is achieved by employment of a strain expressing high levels of the negative regulator of expression in the direction that allows translation of the target gene, as described in the accompanying U.S. application Ser. No. 09/701,626.

The above described method is exemplified in another embodiment of the present invention, namely the cloning and expression of the MseI restriction-modification system.

The present invention also provides novel DNA constructs and novel compositions comprising microbial strains producing MseI restriction endonuclease. The restriction endonuclease of interest in the present invention, MseI, recognizes the DNA sequence 5'-TTAA-3' and cleaves the phosphodiester bond on between the T residues of this recognition sequence to produce a 2 base 5' extension.

In order to overexpress the MseI restriction endonuclease, additional steps beyond the well-known art of the methylase selection procedure (U.S. Pat. No. 5,200,333) are required, including particularly the fine balance of MseI methyltransferase expression to fully protect the host genomic DNA from MseI digestion in vivo while yet not producing so much methyltransferase as to be toxic to the host. A vector, containing the mseIM gene optimized for expression such that full protection against MseI endonuclease is observed even during very rapid (logarithmic stage of) cell growth, is first used to modify an *E. coli* host. This host is then transformed with a compatible vector, such as pVR-25, containing the mseIR gene followed by selection for colonies that contain both vectors on the appropriate antibiotic plates. MseI endonuclease producing constructs are identified by growing individual transformants and assaying for MseI endonuclease activity, (as in Example V below).

The method described herein by which the MseI methylase gene and the MseI restriction endonuclease genes are preferably cloned and expressed in *E. coli* employs the following steps:

1) Cloning of the DNA methyltransferase genes which protect from MseI cleavage.

It is well known that DNA modification methylases recognize and bind to the same nucleotide recognition sequence as the corresponding restriction endonuclease, but instead of breaking the DNA, they chemically modify one or other of the nucleotides within the sequence by the addition of a methyl group. Following this methylation, the recognition sequence is no longer bound or cleaved by the restriction endonuclease. The DNA of a bacterial cell is always fully modified, by virtue of its modification methylase, and it is therefore completely insensitive to the presence of the endogenous restriction endonuclease. In this situation, only unmodified, and therefore identifiably foreign, DNA that is sensitive to restriction endonuclease recognition and attack. The first step of present method is to identify the DNA methyltransferase gene which protects from MseI cleavage. To accomplish this the DNA methylase from *Micrococcus* species (NEB446) can be cloned. Alternatively, a DNA methyltransferase from an R-M system other than the MseI R-M system, but able to protectively modify DNA to prevent digestion by the MseI restriction enzyme can be identified as described in U.S. Pat. No. 5,179,015. In the present invention, three DNA methylases able to protect DNA from digestion by the MseI restriction enzyme were identified.

First, the total genomic DNA was purified from *Micrococcus* species (NEB#446). A random library of this DNA was constructed by partially digesting the DNA with a frequent cutting endonuclease, Sau3AI, to produce fragments of approximately 1 to 10 kilobases (kb) in length. These fragments were ligated into a vector pBR322, previously cleaved with BamHI and dephosphorylated. The ligation reaction was transformed into chemically competent *E. coli* ER2502 cells. The transformants were pooled, and the plasmid was population purified to form the primary plasmid library. An aliquot of these purified plasmids was digested with MseI restriction endonuclease to destroy all plasmids which had not expressed the MseI methylase gene in vivo and thus protected the plasmid DNA from digestion. The digested plasmid pool was transformed again into *E. coli* ER2502 to recover the intact, MseI methylase expressing plasmids. Individual clones were picked, there plasmid DNA was purified and challenged by cleavage with MseI endonuclease. Plasmids which were not cut by MseI contained the MseI methyl-transferase gene.

In a preferred embodiment, the methyltransferase gene is one protecting against the restriction endonuclease MseI obtainable from *Micrococcus* species (NEB#446), and may be selected from among the set of sequences that can encode proteins specified in SEQ ID NO:2, SEQ ID NO:4, and SEQ ID NO:7. These proteins may be encoded for example by those DNA sequences set forth in SEQ ID NO:1, SEQ ID NO:3, and SEQ ID NO:6.

To search for alternative DNA methyltransferases that are able to protect DNA from cleavage by MseI endonuclease, a library of clones from a source of DNA other than *Micrococcus* species may be constructed in a vector containing one or more MseI restriction sites. This library of clones is then selected by one or more rounds of MseI digestion to destroy non-protecting clones followed by transformation of the digested plasmids to recover protected clones. Such a library was created from DNA (designated "environmental DNA") isolated from a sample of a mixed green filament and mat community of prokaryotes growing at 68° C. at Dixie Valley Hot Spring, Nev. Purified enviromental DNA was digested with NsiI endonuclease and ligated into the vector pNEB193 previously cleaved with PstI restriction endonuclease and dephosphorylated. The ligation reaction was transformed into *E. coli* ER2683 by electroporation. The transformants were pooled and the plasmid population was purified to form the primary plasmid library. An aliquot of these purified plasmids was digested to completion with an excess of MseI restriction endonuclease and used to transform ER2683. Plasmids of the resulting transformants were miniprepped and analyzed by MseI restriction enzyme digestion and subsequent agarose gel electrophoresis. 9 plasmids examined were found to be resistant to MseI digestion and each was found to encode one of two different methylase genes that each function to protect DNA from cleavage by MseI. These two methylases were named esaDix4IM (SEQ ID NO:3 and SEQ ID NO:4) and esaDIx5IM (SEQ ID NO:5 and SEQ ID NO:6). Analysis of crude cell extracts prepared from these clones revealed no endonuclease activity. These methyltransferases, or others like them, may be used to protect a host's own DNA and thus enable the successful expression of the MseI endonuclease.

2) Sequence determination of the entire MseI restriction-modification system.

The MseI methylase gene, but not the MseI endonuclease gene, was obtained generally in accordance with the technique referred to as methylase selection (U.S. Pat. No. 5,200,333) as above in step 1. However none of the clones obtained by methylase selection expressed detectable MseI restriction endonuclease activity. A methylase clone was sequenced using standard techniques on an ABI 373 DNA sequencing machine. The MseI methylase gene was identified based on amino acid homology to other N6-adenine methylases. Although the methylase clone did not produce any detectable MseI endonuclease activity, it was speculated that the endonuclease gene was likely located adjacent to the methylase gene. DNA contiguous to the MseI methylase gene obtained from *Micrococcus* species (NEB#446) was therefore amplified from *Micrococcus* species genomic DNA by inverse PCR techniques and sequenced.

To locate and positively identify the MseI endonuclease gene, the N-terminal amino acid sequence of highly purified MseI restriction endonuclease protein obtained from *Micrococcus* species was determined. MseI endonuclease may be purified from *Micrococcus* species (NEB#446) as set forth in Example III below. An open reading frame in which the deduced amino acid sequence matched the N-terminal amino acid sequence of the MseI endonuclease was observed in the DNA sequence obtained by inverse PCR techniques which was located 3' of the methylase gene.

Alternatively, the N-terminal amino acid sequence of MseI restriction endonuclease can be used to design degenerate oligonucleotide primers for PCR amplification of a portion of the MseI endonuclease gene from *Micrococcus* species (NEB#446). The DNA sequence obtained can then be used to guide inverse PCR amplification of the DNA on either side of this original portion of the MseI endonuclease gene, and the mseIM and MseI genes can be identified in this DNA sequence as above. Both methods were used for cloning and sequence determination of the entire MseI restriction-modification system.

3) Fine Optimization of the MseI Methyltransferase Expression

Once the complete genes for the MseI endonuclease and MseI methyl-transferase have been identified (SEQ ID NO:7, SEQ ID NO:8 and SEQ. ID. NO:1 and SEQ ID NO:2, respectively), they may then be manipulated in a variety of ways to provide for expression. Using the methylase constructs obtained as above, expression of the MseI restriction endonuclease gene under T7 promoter control using the pET series of vectors (Novagen Inc., Madison, Wis.) was vigorously attempted but failed to yield a MseI restriction endonuclease producing clone.

A unique combination of methods, including the introduction of a second, controllable promoter before the methylase gene, using a low copy replicon for the endonuclease gene and increasing the copy number of LacI repressor in the host prior to the introduction of the endonuclease gene, was used to control the overexpression of recombinant MseI endonuclease.

It was observed that the methylase constructs obtained by methylase selection did not fully protect the host *E. coli* chromosomal DNA when the cells were rapidly growing in logarithmic phase of growth. In order to increase expression of the methylase, and thus fully protect the host DNA so that mseIR could be introduced successfully into the cells and expressed, the methylase gene was amplified from *Micrococcus* species DNA and cloned into a family of vectors (pNK series, see Example IV below) under the expression of various strength constitutive promoters. In this attempt, no methylase constructs were obtained for the two highest level of expression promoters, due we believe to toxicity to the cell from too much expression of the methylase. Constructs with the two lower level of expression promoters failed to fully protect the host against MseI cleavage when checked at logarithmic phase of growth. In order to increase methylase expression to fully protect the host DNA during rapid growth but remain below the level of toxicity, one of the promoter constructs was subjected to random mutagenesis by error-prone PCR in the promoter region. Mutated clones expressing MseI methylase were selected using the methylase selection technique referenced above, and then individual clones were tested for the ability to fully protect host genomic DNA from MseI cleavage during rapid logarithmic growth by harvesting cells during logarithmic growth, purifying DNA from these host cells and testing for full protection from MseI cleavage. One of the constructs found to fully protect against MseI was then used for the expression of the MseI endonuclease.

This method of modulating expression of a methyltransferase to achieve full protection during all stages of host cell growth may prove applicable to other systems where the endonuclease proves difficult to express, or express instability in a host cell (see, U.S. Pat. Nos. 6,025,179 and 6,048,731).

4) Expression of the MseI Restriction Endonuclease Under the Control of an Inducible Promoter To optimize expression of recombinant MseI of the present invention, inducible or constitutive promoters are well known and may be used to express high levels of an mseIR gene in a recombinant host. Similarly, high copy number vectors, well known in the art, may be used to achieve high levels of expression. In accordance with the present invention, it has been found that a particularly preferred method for expression of MseI restriction endonuclease is an expression vector designed to limit expression of the MseI endonuclease during cell growth prior to induction, such as pVR-24 (New England Biolabs, Inc., Beverly, Mass.). This plasmid contains the segment encoding replicative function (ori), a chloramphenicol-resistance gene (Cm), gene encoding kanamycin resistance which is flanked by restriction endonuclease sites suitable for cloning. The cI857 gene encodes a mutant form of the of the lambda bacteriophage repressor protein, which conditionally binds to DNA sequences (the CI operator) that overlap PL and PR (the lambda bacteriophage major leftward and rightward promoters, respectively). The lacI gene encodes a repressor protein, LacI, that conditionally binds a DNA sequence (the lac operator) which has been constructed to overlap PT7 (bacteriophage T7 RNA polymerase transcriptional promoter). Briefly, at high temperature (42° C.) without IPTG, the antisense promoter is active, while $P_{T7}$ is repressed by LacI. At 30° C. and with IPTG expression occurs from $P_{T7}$ (see FIGS. 11 and 12). At intermediate temperatures and with intermediate IPTG concentrations, intermediate levels of expression can be obtained.

To obtain a stable clone which overexpresses the restriction endonuclease, the host is generally pre-protected from restriction endonuclease digestion. In the present invention this is accomplished by cloning the MseI methylase gene, or another methylase gene that protects against MseI cleavage, such as esaDix4IM or esaDix5IM, expressed on the separate compatible plasmid in a manner providing full protection against MseI cleavage. As shown in the Example V below it was found that the stability of the expression plasmid containing the restriction endonuclease gene construct and/or its mRNA could be improved when the MseI methyltransferase gene is preceded by a DNA fragment encoding a novel promoter sequence. The MseI endonuclease is produced by growing the host containing the MseI endonuclease and the protective methylase gene, inducing with the appropriate expression conditions, harvesting the cells and purifying the MseI endonuclease therefrom.

The invention further provides a process for producing the MseI restriction endonuclease, in which recombinant DNA modification methods are used for transforming a microorganism such that the gene encoding the MseI restriction endonuclease and a gene coding for a DNA methyltransferase which protects the host DNA from MseI cleavage are introduced into said microorganism, the organism is grown under conditions suitable for expression of MseI endonuclease, harvested and the MseI endonuclease is purified therefrom.

Although the above-outlined steps represent the preferred mode for practicing the present invention, it will be apparent to those skilled in the art that the above described -approach can vary in accordance with techniques known in the art.

The following Examples are given to illustrate embodiments of the present invention as it is presently preferred to practice. It will be understood that these Examples are illustrative, and that the invention is not to be considered as restricted thereto except as indicated in the appended claims.

The references cited above and below are herein incorporated by reference.

EXAMPLE I

Cloning of the MseI Methyltransferase Gene (mseIM)

*Micrococcus* species (NEB#446) was grown overnight in 1 L of LB broth, the cells were harvested and genomic DNA was isolated using Qiagen Genomic-tip 100/G Genomic DNA Purification Kit (Cat. No. 10243) according to the manufacturer's instructions. Genomic DNA was partialy digested with Sau3AI to produce fragments from 1 to 10 kb, and 20 μg of this cleaved genomic DNA was ligated with 3 μg of BamHI-digested and dephosphorylated pBR322. The ligation mixture was transformed into *E. coli* strain ER2502. Approximately 100,000 transformants were obtained. The transformants were pooled, grown in 500 ml LB broth containing 100 μg/ml ampicillin, and the plasmid population was purified to form the primary plasmid library. 2 micrograms of this plasmid library was digested to completion with an excess of MseI restriction endonuclease and used to transform ER2505. Plasmids of the resulting transformants were subjected to a second round of selection. 80 transformants were obtained and the plasmid DNA of 16 of these was analyzed by MseI restriction enzyme digestion and subsequent agarose gel electrophoresis. 14 out of 16 plasmids examined were found to be resistant to MseI digestion and found to carry the same mseIM gene (SEQ ID NO:1, SEQ ID NO:2) on a Sau3AI fragment of approximately 1.6 kb. Analysis of crude cell extracts prepared from those 14 clones revealed no MseI activity.

EXAMPLE II

Cloning two DNA Methylases from an Environmental DNA Sample that Protect DNA from Cleavage by MseI Endonuclease.

To search for alternative DNA methyltransferases that are able to protect DNA from cleavage by MseI endonuclease, a library of clones from a source of DNA other than *Micrococcus* species (NEB446) may be constructed in a vector containing one or more MseI restriction sites. This library of clones is then selected as above by one or more rounds of MseI digestion to destroy non-protecting clones followed by transformation of the digested plasmids to recover protected clones, as in Example I above. Such a library was created from DNA isolated from a sample of a mixed green filament mat community of prokaryotes growing at 68° C. at Dixie Valley Hot Spring, Nev. 2 micrograms of the DNA was digested with NsiI endonuclease and ligated into 1 microgram of the vector pNEB193 previously cleaved with PstI and dephosphorylated. The ligation reaction was transformed into *E. coli* ER2683 by electroporation and approximately 1,000,000 transformants were obtained. The transformants were pooled, grown in 500 ml LB broth containing 100 g/ml ampicillin, and the plasmid population was purified to form the primary plasmid library. 1 microgram of this plasmid library was digested to completion with an excess of MseI restriction endonuclease and used to transform ER2683. Plasmids of the resulting transformants were miniprepped and analyzed by MseI restriction enzyme digestion and subsequent agarose gel electrophoresis. 9 plasmids examined were found to be resistant to MseI digestion and were found to encode one of either two different methylase genes that both function to protect DNA from cleavage by MseI. These two methylases were named esaDix4IM and esaDix5IM (SEQ ID NO:3, SEQ ID NO:4 and SEQ ID NO:5 and SEQ ID NO:6). Analysis of crude cell extracts prepared from these clones revealed no endonuclease activity. These methyltransferases, or others like them, may be used to protect a host's own DNA and thus enable the successful expression of the MseI endonuclease.

EXAMPLE III

Identification and Sequence Determination of the MseI Restriction Endonuclease Gene Using N-terminal Amino Acid Sequence and DNA Sequence Adjacent to the MseI Methylase Obtained by the Inverse PCR Method.

A) Purification of the MseI Restriction Endonuclease from Micrococcus Species to Near Homogeneity:

*Micrococcus* species (NEB#446) cells were propagated in LB media at 30° C. The cells were harvested by centrifugation after 20 hours growth and stored at −70° C. until used. All of the procedures were performed on ice or at 4° C. The MseI endonuclease was purified following the same scheme as in Example VI. Approximately 10,000 units of MseI activity were purified to near homogeneity. 16 µl of the peak fraction was loaded onto an SDS-PAGE protein gel and subjected to electrophoresis. The gel was stained with Coomassie blue R-250 and a prominent band at approximately 21 kD corresponding to the MseI restriction endonuclease activity was observed.

B) Amino Terminal MseI Protein Sequence:

The MseI restriction endonuclease, prepared as described, was subjected to electrophoresis and electroblotted according to the procedure of Matsudaira (Matsudaira, P., *J. Biol. Chem.* 262:10035–10038 (1987), with modifications as previously described (Looney, et al., *Gene* 80:193–208 (1989)). The membrane was stained with Coomassie Blue R-250 and the protein band of approximately 21 kd was excised and subjected to sequential degradation on an Applied BioSystems Division, Perkin-Elmer Corporation (Foster City, Calif.) Model 407A gas phase protein sequencer (Waite-Rees, et al., *J. Bacteriol.* 173:5207–5219 (1991)). The first 25 residues of the 21 kD protein corresponded to (Met)-Thr-His-Glu-Pro-Thr-Asp-Asp-Pro-Asp-Phe-Ile-Val-Met-Ala-Ala-Ser-Ala-Xxx-Asn-Leu-Ala-Asp-Xxx-Tyr (SEQ ID NO:10). This data was used to compare with amino acid sequence deduced from the DNA sequence adjacent to the methylase gene to identify the endonuclease gene.

C) DNA Sequence Determination Adjacent to the mseIM Methylase:

Template preparation for inverse PCR amplification: 1 µg of *Micrococcus* species (NEB#446) DNA was digested with 10 units of HaeII restriction endonuclease in 1×NEBuffer #4 in a 50 µl reaction volume for 1 hour at 37° C. The HaeII enzyme was heat inactivated by incubating at 75° C. for 20 minutes. The HaeII digested DNA was circularized by adding 50 µl 10×T4 DNA ligase buffer and 400 µl dH$_2$O, followed by 5 µl (2000 NEB units) T4 DNA ligase (NEB#202) and incubating at 16° C. for 16 hours. A portion of this circularization ligation reaction was then used as the template for subsequent inverse PCR reactions.

Primers MseI-IP1 and MseI-IP2 of sequences shown below were synthesized. These primers hybridize within the MseI endonuclease gene and are oriented in the opposite direction relative to each other.

Primer MseI-IP1
5'-CTTCTGCAGCCGATTTCATAGTGATGGC-3' (SEQ ID NO:11)
Primer MseI-IP2
5'-GTTCTGCAGATCGGGATCATCCGTCGG-3' (SEQ ID NO:12)

In the reaction that was successful in amplifying the product, a reaction mix was made by combining:
10 µl of 10×Vent® reaction buffer
6 µl of 4 mM dNTP solution
5 µl of primer MseI-IP1 at 10 µM concentration
5 µl of primer MseI-IP2 at 10 µM concentration
3 µl of 100 mM MgSO$_4$ (5 mM Mg$^{++}$final concentration)
12.5 µl of circularized DNA template (aproximately 25 ng)
58 µl dH$_2$O
2 µl (4 units) of Vent® Exo$^-$polymerase NEB#257

The PCR amplification conditions were: 95° C. for 3 minutes for one cycle, followed by 4 cycles of 95° C. for 30 seconds, 52° C. for 30 seconds and 72° C. for 1.5 minutes, followed by 20 cycles of 95° C. for 30 seconds, 62° C. for 30 seconds and 72° C. for 1.5 minutes. 10 µl of the PCR reaction was analyzed by electrophoresis on a 0.8% agarose gel.

An approximately 1350 bp product was observed in the HaeII circular template PCR reaction. The product was gel purified and suspended in 25 µl DNA (1×TE) buffer. This PCR product was then sequenced on an ABI 373 automated sequencing system according to the manufacturer's instructions, using the PCR primers above as the sequencing primers. Additionally, the MseI endonuclease region was PCR amplified in a like reaction with the following primers and the PCR product was sequenced.

Primer MseI-IP3
5'-GGTTCTGCAGTTAAGGAGGTTTAACATATGATAT-GACCCACGAACCGACG GATG-3' (SEQ ID NO:13)
Primer MseI-IP4
5'-GTTGGATCCGTCGACGCTTCTCGGCGTACCGAG-CG-3' (SEQ ID NO:14)

The MseI endonuclease gene is identified by comparing the amino acid translation of DNA sequences adjacent to the MseI methylase gene with the amino acid sequence data obtained from N-terminal amino acid sequencing of the MseI endonuclease. An open reading frame oriented in the same direction as the MseI methylase gene and overlaping the methylase gene by 7 amino acid residues was found in which the first 25 amino acids coded for in the DNA sequence matched the amino acid sequence determined from the MseI endonuclease protein.

Sequencing of the insert carrying the MseI methylase and restriction endonuclease genes was performed using GPS®-1 of the Genome Priming System (New England Biolabs, Beverly, Mass.). GPS®-1 contains a modified Tn7 with the nptII gene for resistance to kanamycin, and insertions were generated in vitro in pVR-18 and pNEB193 containing part of the MseI methylase gene according to the instructions of the manufacturer (New England Biolabs, Beverly, Mass.). These insertions were then sequenced using an ABI 373 automated sequencing system according to the manufacturer's Instructions, using the primers included in GPS®-1 kit (Primer S and Primer N for the left and right end of the Transprimer, respectively)

EXAMPLE IV

Optimization of the MseI M Expression

1) Placing the MseI Methylase Gene Under Different Strength of Constitutive Promoters To achieve a range of constitutive expression of the MseI methylase, a related family of pNK vectors (generous gifts from N. Kleckner) containing constitutive promoters of different strengths was utilized. These plasmids contain either the WT or mutated pHis promoters upstream of a BamHI site and are derivatives of the RS415 plasmid (Simons, et al. *Gene*, 53 (1987) 85–96). Their designations and promoter strength are as follows:

| No. | Plasmids | Promoter Strength |
|---|---|---|
| 1 | pNK1707 (wildtype) | 1× |
| 2 | pNK2213 | 20× |
| 3 | pNK1786 | 100× |
| 4 | pNK2138 | 1070× |

The above plasmids were digested by BamHI, MunI and BanII and the vector backbones containing the constitutive promoters were gel purified. (The BanII digest was included to aid in gel purification of the vector backbone by eliminating a similarly sized plasmid fragment.)

To prepare the MseI methylase gene for insertion downstream of the constitutive promoters described above, PCR was done using Vent® DNA polymerase, 1× ThermoPol buffer, 4 mM MgSO$_4$, 80 ng of pVR19 plasmid (R. Valsvila) containing the MseI methylase gene as the template in a 100 μl PCR reaction, and primers introducing an upstream BamHI site 5'-GAACCGGATCCGACCCTGA-GTGAGMCATGCC-3' (SEQ ID NO:15) and a downstream MfeI site 5'-AGGTCGCAATTGCCAGG GGTCGTCTTC-ACTCGCTAC-3' (SEQ ID NO:16) with respect to the methylase gene. Twenty-five cycles were done consisting of 10 sec at 95° C., 60 sec at 60° C. and 75 sec at 72° C. The resulting 1019 bp PCR product was purified using a QiaQuick PCR purification protocol, digested sequentially by BamHI and MunI, and purified once again using the QiaQuick PCR purification protocol.

The MseI methylase gene was ligated into all four BamHI-MunI vector backbones, transformed into ER2688 cells, and plated on Luria-Bertani (supplemented with 1 gram glucose and 1 gram MgCL$_2$ per liter; subsequently referred to as supplemented LB) agar plates. However, attempts to place the MseI methylase under the highest two levels of expression failed, assumingly due to instability from high levels of methylation in the cells. Constructs containing the lower two levels of expression (pNKR1707MseIm, pNKR2213MseIm did not result in full methylation of the cellular DNA, as judged by susceptibility of purified plasmid DNA from these cells to restriction by MseI (1 μg plasmid DNA in 50 μl volume, 20 units MseI, 1 hour at 37° C.).

2) Construction of a Library of Randomly-mutagenized Constitutive Promoters by Error-prone PCR To find an intermediate level promoter construct for the MseI methylase between that of pNKR2213MseIm and the apparently unstable pNKR1786MseIm, the constitutive promoter region was subjected to random PCR mutagenesis and selection. The mutagenesis protocol employed high levels of Taq DNA polymerase (5 units/100 μl reaction volume), unequal dNTP pools (1.2 mM dCTP and TTP; 0.2 mM dATP and dGTP), high levels of MgCl$_2$ (7 mM), presence of MnCl$_2$ (0.5 mM), 2 ng of the pNKR1707MseIm per 100 μl volume and high PCR cycle numbers (35). The primers flanked the MseI methylase gene at the AgeI and BamHI restriction sites respectively 5'-GCGATACAGACCGG-TTCAGACAGGATAAAG-3' (SEQ ID NO: 17) and 5'-GGTCGGATCCGGCGATACAGCGAG-3' (SEQ ID NO:18).

After PCR, the mutated promoter copies were restricted by AgeI and BamHI, gel purified with a Qiagen gel purification kit, and ligated into a AgeI-BamHI restricted pNKRMseIm construct that had been purified away from its endogenous constitutive promoter. Following electroporation into competent ER2688 cells, 20,000 colonies were achieved. These colonies were pooled and the plasmids were purified using a Qiagen purification protocol. This constituted a library of randomly mutagenized constitutive promoters, upstream of the MseI methylase gene.

3) Selection of Clones Yielding Plasmids Resistant to MseI Restriction

To select for plasmids possessing a mutated constitutive promoter resulting in a stable, high level of methylation, 5 μg of the plasmid library was challenged by MseI restriction (5 μg DNA, 50 units MseI for 4 hrs at 37° C., followed by a 20 min incubation at 65° C. to inactivate the MseI restriction endonuclease. A portion of the challenged pool (250 ng) was transformed into calcium-competent ER2688 cells and plated on supplemented LB agar plates and grown overnight at 37° C. This resulted in 63 colonies.

Six of these 63 colonies were randomly selected for further individual examination; after overnight growth in 10 ml supplemented LB medium, plasmid DNA was purified using a Qiagen Qia-prep spin miniprep protocol. When 100 ng of the purified plasmid DNA was challenged with 20 units of MseI for 30 minutes at 37° C., all 6 were found to be fully restricted, indicating an inadequate level of methylation.

The remaining 57 colonies were pooled and a plasmid purification was done using a Qiagen plasmid purification protocol. From this plasmid pool, 50 ng was subjected to a longer (overnight) 50 unit MseI challenge, followed by a 20 min incubation at 65° C. to inactivate the MseI restriction endonuclease. A portion of the challenged pool (4 ng) was transformed into calcium-competent ER2688 cells, plated on supplemented LB agar plates and grown overnight at 37° C. This resulted in 13 colonies.

Nine of these 13 colonies were randomly selected for further individual examination; after overnight growth and plasmid purification as previously described, 7 of the 9 were found to be fully methylated when 1 μg plasmid DNA was incubated with 50 units MseI In a 50 μl reaction volume overnight at 37° C.

To further establish the level of methylation present in the cells, the 7 colonies were harvested for plasmid purification during the logarithmic phase of culture growth (cells were harvested 4 hours at 37° C. after a 1:100 dilution of an overnight culture into fresh supplemented LB growth medium). Such cells would be expected to be replicating their DNA at such a rate that methylation by an expressed MseI methylase might be unable to achieve complete methylation. Plasmid DNA was purified from these logarithmically growing cultures using Qiagen Qia-prep purification protocols and 0.5 μg of this plasmid DNA was incubated overnight at 37° C. with 50 units MseI. Using this more difficult methylation standard, 3 of the 7 colonies were fully protected (methylated) and resistant to restriction.

The three clones (#4, #9 and #10) resulting in a stable and full level of MseI methylation had their promoter regions examined by mapping with AgeI and BamHI, and sequencing using a primer with an annealing position upstream of the promoter region. (5'-GGATCTTCCAGTG-GTGCATGAACG-3' (SEQ ID NO:19). Two of the 3 clones (#9 and #10) were identical; thus the two step selection process described resulted in finding two independent promoters that yield a stable, full level of MseI methylation.

Unexpectedly both promoter #4 and promoter #9/#10 were not mutagenized constitutive promoters as had been the experimental design, but instead were AgeI-BamHI E. coli sequences that must have originated from the low level of E. coli DNA contamination present in the plasmid preparations.

The #4 promoter, by AgeI/BamHI, mapping appeared to be approximately 1000 bp in length; by sequencing, the first 438 bp were identical to E. coli K-12 MG1655 section 349 (Accession No. AE000459), base # 7813–8251. Upon examination of the sequence data, a BamHI site was found at base #8814, which would yield the AgeI-BamHI E. coli fragment of 1002 bp. This E. coli sequence contains the 5' end of the yigW_2 orf and two predicted promoters, one of which is oriented in the same direction as the MseI methylase (#8672–8704).

The #9/#10 promoter mapping appeared, by AgeI/BamHI, to be approximately 420 bp in length; by sequencing, the promoter was identical to E. coli K-12 MG1655 section 41 (Accession No. AE000151), base # 2511–2998. This defines a 488 bp AgeI-BamHI E. coli fragment that contains the 5' end of the cof orf and two predicted promoters oriented in the same direction as the MseI methylase at positions #2605–2632 and #2714–2742. This #9/#10 sequence was used for further work.

4) Further Optimization of MseI Methylase Expression

Using the strategy described above, a level of MseI methyltransferase expression which allowed expression of the MseI endonuclease in plasmid pVR-25 was achieved. Unexpectedly, while the ER2566 host carrying the optimized MseI methylase (#9 above) and the MseI endonuclease in plasmid pVR-25 expressed MseI endonuclease when first transformed and grown, the MseI was not stably maintained when this construct was stored in glycerol at −70° C.

The MseI methylase construct was further modified to achieve greater MseI modification of the host. As described above, the attempts to place the MseI methylase under the highest two levels of constitutive expression failed, presumably due to instability from high levels of methylation in the cells. To achieve a maximum tolerated level of methylation, a new M.MseI expression plasmid, pVR-26, was constructed. pVR-26 was constructed by inserting a second promoter, derived as described in (3) above (see Table 1). This was done by cutting out a 1.244-kb DNA fragment containing the M. MseI coding region (mseIM gene) and upstream promoter from plasmid pNKR1707 mseIM-9 (digested with PmeI and MfeI) and inserting it just downstream of the $P_{lacUV5}$ promoter in vector pNEB193 (New England Biolabs, Inc., Beverly, Mass.) cut with EcORI and HincII. Another MseI methylase construct, pVR-27, was made by deleting a 0.379-kb PmeI-AflIII fragment containing the $P_{lacUV5}$ promoter and

TABLE 1

Summary of plasmids and *Escherichia coli* hosts used for optimizing recombinant MseI production

| Strain<br>Host | MseRM1<br>ER2566 | MseRM2<br>ER2566 | MseRM3<br>ER2833 | MseRM4<br>ER2833 | MseRM5<br>ER2566 | MseRM6<br>ER2833 |
|---|---|---|---|---|---|---|
| pVR-25<br>PVR-24 with mseIR. At high temperature (42° C.) without IPTG, the antisense promoter is active, while $P_{T7}$ is repressed by LacI. At 30° C. and with IPTG expression occurs from $P_{T7}$. $Cm^R$, ~10–15 copies/cell | + | + | + | + | + | + |
| pNK1707mseIM-9<br>pNK1707 with a mseIM gene and a fragment of *E. coli* chromosomal DNA containing promoter. $Ap^R$, ~40–50 copies/cell | + | | + | | | |
| pVR-26<br>pNEB193 with mseIM fragment and upstream promoter region (PmeI-MfeI fragment) from pNK1707mseIM-9. $P_{UV5}$ and $O_{lac}$ are active. $Ap^R$, ~500 copies/cell. | | | + | | + | |
| pVR-27<br>pVR-26 with a PmeI-AflIII | | | | | + | + |

TABLE 1-continued

Summary of plasmids and *Escherichia coli* hosts used for optimizing recombinant MseI production

| Strain<br>Host | MseRM1<br>ER2566 | MseRM2<br>ER2566 | MseRM3<br>ER2833 | MseRM4<br>ER2833 | MseRM5<br>ER2566 | MseRM6<br>ER2833 |
|---|---|---|---|---|---|---|
| deletion. The $P_{UV5}$ and $O_{lac}$ are deleted.<br>$Ap^R$, ~500 copies/cell | | | | | | |
| pCEF-8<br>pSYX20 (pSC101 origin) with T7 lysozyme gene cloned into SalI site in oposite direction to the $P_{Tet}$. $Kn^R$, ~2–5 copies/cell | + | + | + | + | + | + |
| $lacI^Q$ | | | + | + | | + |
| LacI copies/cell | 110–160 | 110–160 | 210–260 | 210–260 | 110–160 | 210–260 |
| $O_{lac}$ copies/cell | 13–18 | ~500 | 13–18 | ~500 | 13–18 | 13–18 |
| Drug resistace | $Ap^R, Cm^R,$<br>$Kn^R$ | $Ap^R, Cm^R,$<br>$Kn^R$ | $Ap^R, Cm^R,$<br>$Kn^R$ | $Ap^R, Cm^R,$<br>$Kn^R$ | $Ap^R, Cm^R,$<br>$Kn^R$ | $Ap^R, Cm^R,$<br>$Kn^R$ | lacI operator form pVR-26. The pVR-26 mseIM methylase expressing vector allowed the stable expression of MseI endonuclease.

EXAMPLE V

Optimization of the MseI Restriction Endonuclease Expression

1) Expression Vector Construction

As known very well in the art, restriction endonucleases are cytotoxic proteins. Attempting to clone a toxic gene into a plasmid designed to facilitate high expression is, in many cases, extremely difficult. One especially preferred plasmid for expressing cytotoxic genes is pLT7K (Kong, et al., *Nucl. Acids Res.* 28:3216–3222 (2000)). This plasmid contains the segment encoding replicative function (ori), a gene encoding β-lactamase, and a gene encoding kanamycin resistance which is flanked by restriction endonuclease sites suitable for cloning. The cI857 gene encodes a mutant form of the of the lambda bacteriophage repressor protein, which conditionally binds to DNA sequences (the CI operator) that overlap PL and PR (the lambda bacteriophage major leftward and rightward promoters, respectively). The lacI gene encodes a repressor protein, LacI, that conditionally binds a DNA sequence (the lac operator) which has been constructed to overlap PT7 (bacteriophage T7 RNA polymerase transcriptional promoter). Briefly, at high temperature (42° C.) without IPTG, the antisense promoter is active, while $P_{T7}$ is repressed by LacI. At 30° C. and with IPTG, expression occurs from $P_{T7}$.

Figure 11:
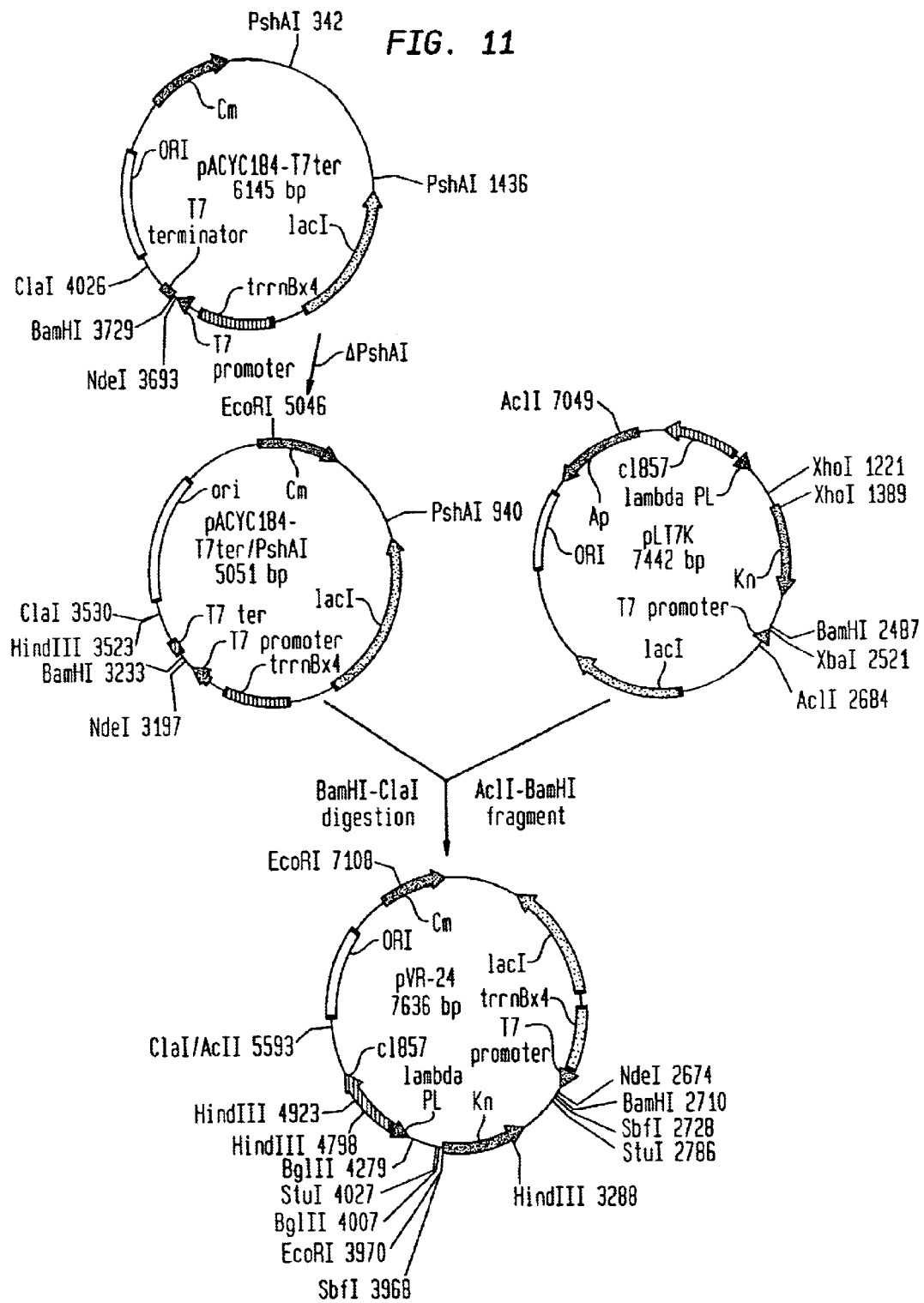
FIG. 11 shows the construction of the pVR-24 expression vector.
Figure 12A:
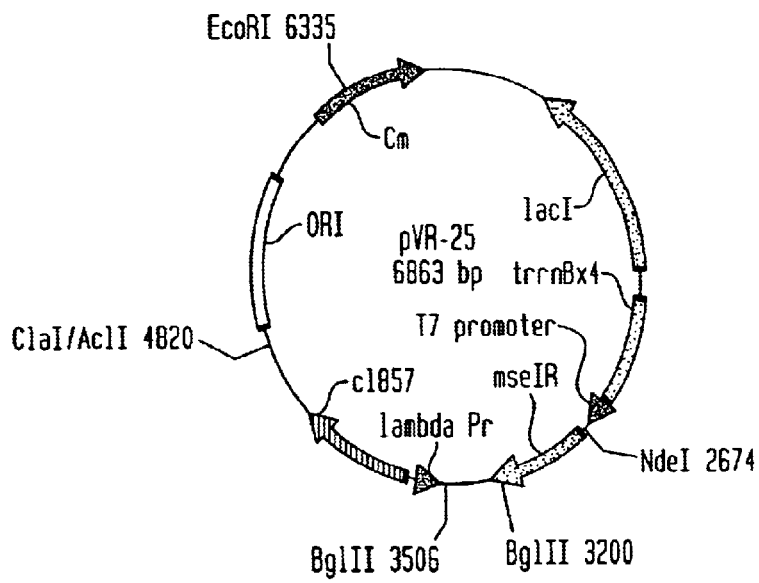
FIG. 12A shows a restriction map of pVR-25 encoding the MseI restriction endonuclease gene.
Figure 13:
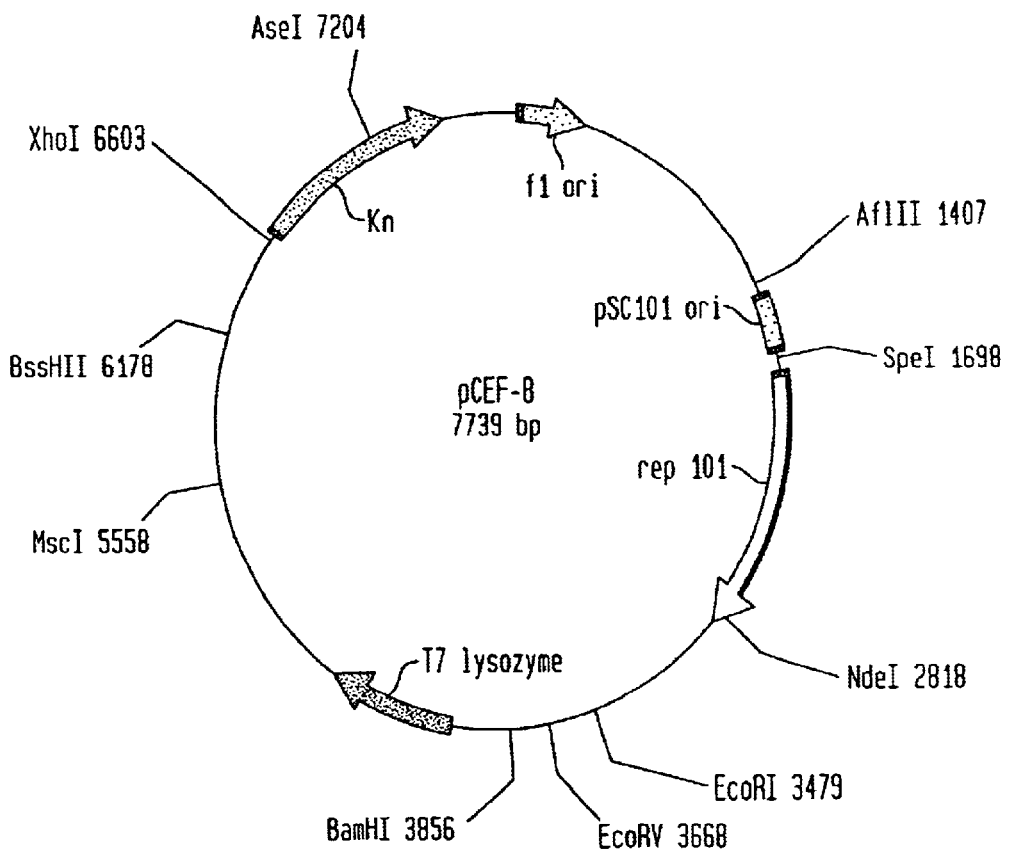
FIG. 13 shows a restriction map of pCEF-8 encoding T7 lysozyme gene.
Figure 12B:
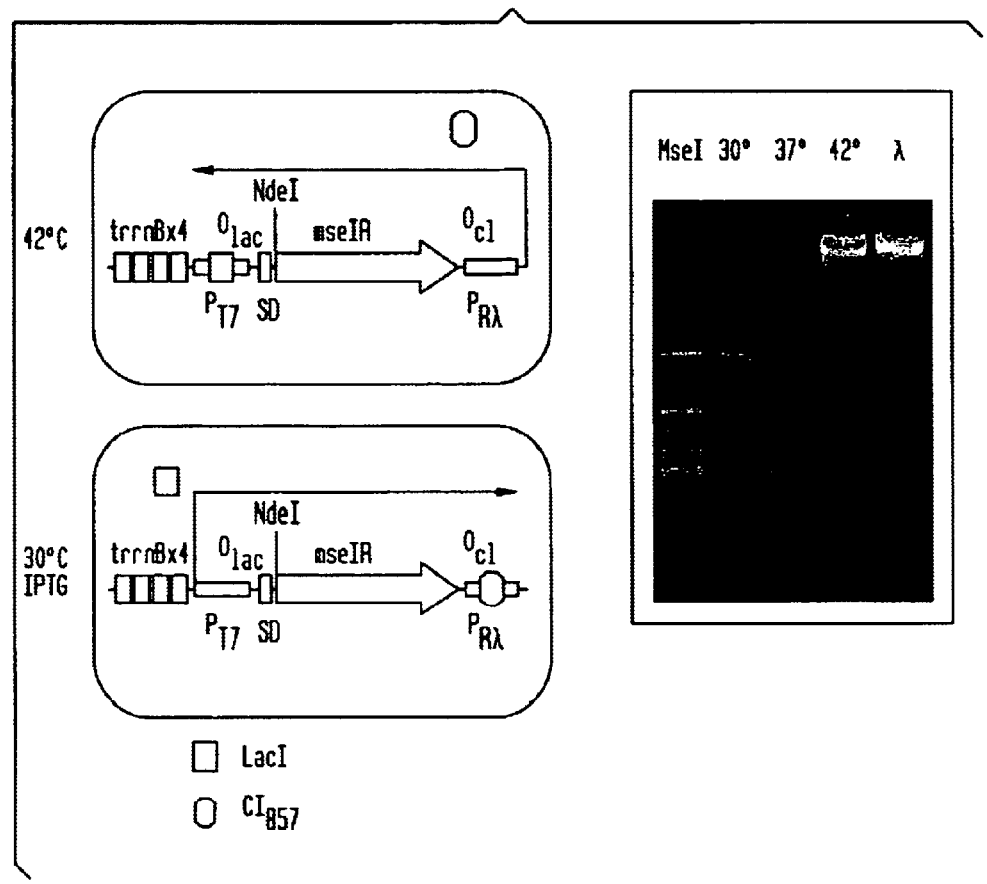
FIG. 12B shows the mechanism of action of the tight regulatory system in pVR-25 for cloning genes encoding cytotoxic proteins.
Figure 15:
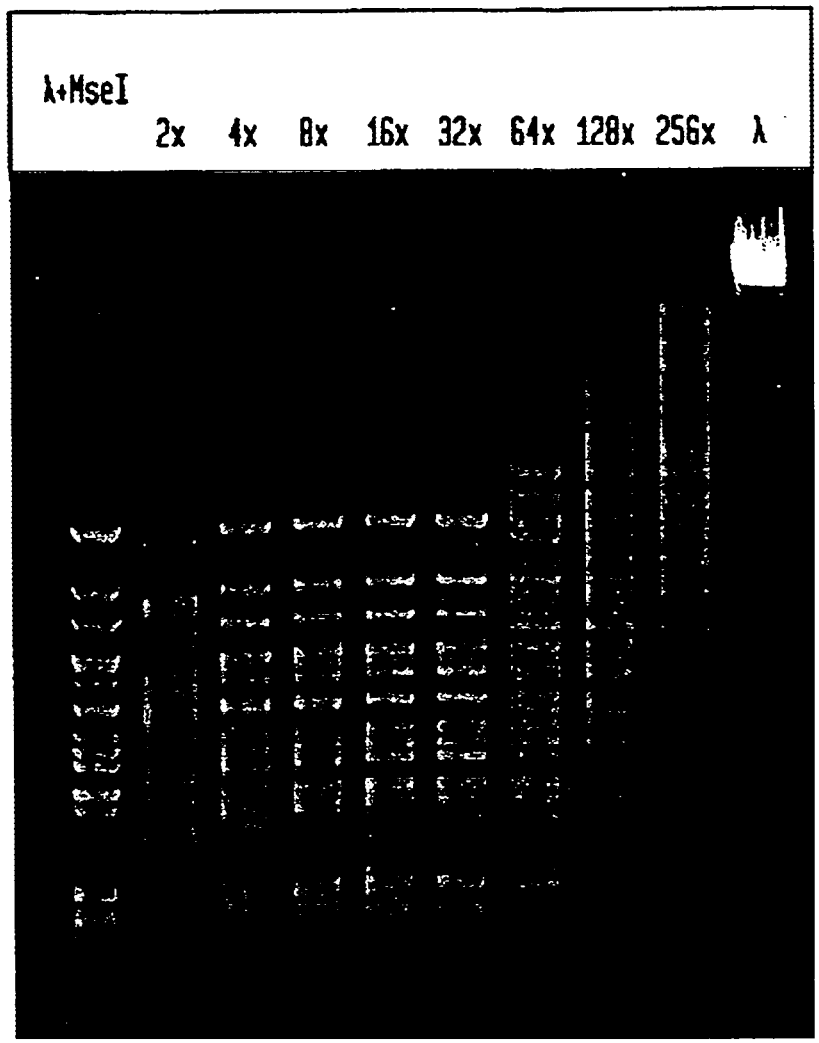
FIG. 15 shows an assay of MseI restriction endonuclease activity in crude cell extracts made from E. coli strain MseRM4 (NEB #1284) after growth in the 100-liter fermenter.

To adapt the pLT7K for overexpression of MseI restriction endonuclease gene, an NdeI restriction endonuclease site and ribosome binding site were introduced. Additionally, the colEI replicon was changed to the p15A replicon and copy number was decreased 3 times (from ~50 to ~15). To acomplish this, pLT7K was digested with Ac/I and BamHI. The resulting 1.2-kb fragment containing cI857, the lambda PL, Kn resistance gene and the T7 promoter was isolated from an agarose gel using Qiagen QIAquick Gel Purification Kit (Cat. No. 28704) and ligated into pACYC184T7terΔPshAI vector that was previously digested with ClaI and BamHI. The pACYC184-T7terΔPshAI is a PshAI deletion derivative of pACYC184-T7ter. This construct was designated pVR-24 (FIG. 11).

The open reading frame (ORF) for the mseIR gene was amplified by PCR with a set of forward (5' AGACTCCCC <u>CATATG</u>ACCCACGAACCGACGGATG 3' (SEQ ID NO:20) and reverse (5' GGGTGGTCCCGCTAGCTATT-AGTAGGGACCGGGG 3' (SEQ ID NO:21) primers, where the underlined bases show the positions of the NdeI cleavage site for the forward primer. PCR was performed using Vent® DNA polymerase, 1×ThermoPol buffer, 500 ng of *Micrococcus* species (NEB#446) chromosomal DNA as the template in a 100 μl PCR reaction, and primers. Twenty-five cycles were done consisting of 15 sec at 95° C., 60 sec at 68° C. and 45 sec at 72° C. The resulting 700 bp PCR product was purified using a QiaQuick PCR purification protocol, treated with Kienow fragment, digested by NdeI, and purified once again using the QiaQuick PCR purification protocol.

The resultant 700-bp NdeI-Blunt end fragment, containing MseI restriction endonuclease gene, was ligated into pVR-24 vector digested with NdeI and StuI and ligation mixture was transformed into *E. coli* ER2502 cells, previously modified with the MseI methylase gene construct pNKR1707MseIm-9. Out of 18 individual transformants analyzed, three contained mseIR gene. After sequencing the DNA insert containing MseI restriction endonuclease gene, one recombinant plasmid, pVR-25, was selected for producing the MseI restriction endonuclease.

2) Strain Construction

To increase LacI repressor copy number in the host, the strain ER2833 (T7lacIq strain) was constructed as described in U.S. application Ser. No. 09/689,359, now U.S. Pat. No. 6,569,669.

3) Optimization of MseI Restriction Endonuclease Overexpression in *E. coli* Combining Different Hosts and Plasmids Expressing Different Levels of MseI Methylase.

For optimization of MseI restriction endonuclease overexpression in *E. coli*, the pVR-25 plasmid was transferred into the expression strain ER2566/pCEF-8, which was preprotected against MseI endonuclease auto-digestion by carrying one of these MseI methylase expressing plasmids (pNKR1707MseIm-9, pCR-26 and pVR-27). ER2566/pCEF-8 is a host strain containing a chromosomal copy of the gene for T7 RNA polymerase under control of the inducible lac promoter and a pSYX20 based plasmid, pCEF-8, which specifies low levels of T7 lysozyme, a natural inhibitor of T7 RNA polymerase. For additional information, see Moffatt, B. A., and Studier, F. W., "T7 Lysozyme inhibits transrciption by T7 RNA polymerase," Cell, 49:221–227 (1987). In uninduced cells, lysozyme reduces the basal activity of the T7 RNA polymerase and increases the range of target genes that can be stably maintained in the expression host. In addition, another expression strain, ER2833/pCEF-8 was used, which has an copy of lacIq gene on the F' episome.

Overall, six strains were used of MseI restriction endonuclease expression studies in *E. coli* (Table 1). All strains contain pVR-25 plasmid, expressing MseI restriction endonuclease, and pCEF-8 plasmid which encodes a T7 bacteriophage lysozyme gene. A variety of growth conditions were employed to grow transformed host cells to select for higher yields of MseI restriction endonuclease. The preferred medium in optimization experiments was Luria-Bertani (supplemented with 1 gram glucose and 1 gram MgCL2 per liter; subsequently referred to as supplemented LB) media.

The growth conditions were as follows:

MseRM1: cells from an individual colony were grown in 0.5 liter of LB medium at 42° C. for 8 h, after which IPTG was added to 0.2 mM final concentration to induce the T7 RNA polymerase and cells were grown overnight (15 h) at 30° C. Antibiotics were added as needed: 30 μg of kanamycin per ml, 100 μg of ampicillin per ml, and 30 μg of chloramphenicol per ml. Finally, cultures were harvested by centrifugation and frozen at −20° C.

MseRM3: for each experiment, cells from an individual colony were grown in 0.5 liter of LB medium at 30° C. overnight (17 h), after which IPTG was added to 0.2 mM final concentration to induce T7 RNA polymerase and cells continued to grow for 4 h. Antibiotics were added as needed: 30 μg of kanamycin per ml, 100 μg of ampicillin per ml, and 30 μg of chloramphenicol per ml. Finally, cultures were harvested by centrifugation and frozen at −20° C.

MseRM4, MseRM5 and MseRM6: bacterial cultures were kept as frozen stock solutions at 70° C. in 50% glycerol. Cultures used for seed inoculation were streaked onto LB medium plates containing the appropriate antibiotics to obtain single colonies. An individual colony was resuspended in 1 ml of LB medium and inoculated into a 1000-ml flasks containing 500 ml of LB medium supplemented with 30 μg of kanamycin/ml 100 μg of ampicillin/ml, and 30 μg of chloramphenicol/ml. Cells were grown overnight (16 h) in a shaking incubator at 37° C. and 250 rpm. Thereafter, IPTG was added to a final concentration of 0.2 mM. Cells were cultivated for another 4 h and then were harvested by centrifugation at 8,000 g for 5 min at 4° C. and frozen at −20° C.

Two preferred restriction endonuclease assays for identifying high-level expression clones were used.

Sonication method: induced cultures (500 ml) were harvested and resuspended in 20 ml sonication buffer containing 10 mM Tris.HCl (pH 7.5) and 1 mM EDTA. Cells were sonicated on ice by four 30 second blasts with a macro-tip probe. A portion of the crude extract was added to lambda DNA (1 μl) in NEBuffer 2 buffer (50 μl) and incubated for 1 hour at 37° C. DNA was fractionated by 0.8% gel electrophoresis and visualized by EtBr staining.

EXPRESS method: one ml of an overnight or induced culture (10–500 ml) was harvested and resuspended in 0.2 ml buffer containing 50 mM TRIS-HCl, pH 7.5 and 25% (vol/vol) sucrose and mixed until the solution was homogenous. 11 μl of 200 mM EDTA, pH 8.0 plus 200 μl of freshly-prepared 10 mg/ml lysozyme in 0.25M Tris-HCl (pH 8.0) were added and the solution was incubated on ice for 5 min. 11.5 μl of 1 M $MgCl_2$ and 24.2 μl of 5% (vol/vol) Brij-58 were then added. The solution was gently mixed and incubated in room temperature for 15 min. After incubation the crude cell lysate was centrifuged at maximum speed in a microcentrifuge for 15 min at 4° C. The supernatant was pipetted off into a new eppendorf tube and stored on ice until needed. Lambda DNA substrate (1.0 μg) was digested in MseI reaction buffer buffer (NEBuffer 2) with serial dilutions of cell extract for 1 hour at 37° C. degree. DNA was fractionated by electrophoresis and visualized by EtdBr staining. Activity was determined by the presence of the appropriate size bands associated with a MseI digestion of lambda DNA.

The results of optimization of MseI restriction endonuclease expression are summarized in Table 2.

MseRM1 strain gave a variable yield of MseI restriction endonuclease (0.08–0.5×$10^6$ U/g wet cells). Cells grew slowly and the lag time was exceptionally long.

To enhance the stability and reproducibility of lac-based recombinant expression systems, the new host strain ER2833 (U.S. applicaticn Ser. No. 09/689,359), U.S. Pat. No. 6,569,669 was constructed, which has an copy of $lacI^q$ gene on the F' episome. Indeed, the expression stability and plasmid maintenance in the $lacI^q$ host (MseRM3) was greatly enhanced: the yield of MseI restriction endonuclease was 0.5–1.4×$10^6$ U/g wet cells. The MseI restriction endonuclease purified from this strain (see Example VI) was substantially free of non-specific endonuclease and exonuclease and the final yield was

TABLE 2

Summary of optimization of MseI restriction endonuclease expression in *E. coli*

| Strain | Induction Conditions | Yield (U/g) | Comments |
|---|---|---|---|
| MseRM1 | 42° C. 8 h (~40 Klett), shift to 30° C. overnight | 0.08–0.5 × $10^6$ | Difficult to repeat results. No activity from frozen culture |
| MseRM2 | | | ER2566/pVR-26 grew very slowly, impossible to make competent cells |
| MseRM3 | 30° C. 37° C. overnight (~100 Klett), IPTG (0.2 mM) 4 h | 0.5–1.4 × $10^6$ | No activity from frozen culture. The enzyme prep gave ~150,000 U/g |
| MseRM4 | 37° C. overnight (~100 Klett), shift to 30° C. + IPTG (0.2 mM) 4 h | 3.3–8.6 × $10^6$ | This strain gave stable results from frozen culture, high MseI yield |
| MseRM5 | 37° C. overnight (~100 Klett), shift to 30° C. + IPTG (0.2 mM) 4 h | 1.5–3.4 × $10^6$ | This strain gave stable results from frozen culture, but has less MseI yield than MseRM4 |
| MseRM6 | 37° C. overnight (~100 Klett), shift to 30° C. + IPTG (0.2 mM) 4 h | 3.3–3.8 × $10^6$ | This strain gave stable results from frozen culture, but has less MseI yield than MseRM4 |

[a]Resuspend an overnight colony (plated on 42° C.) in 1 ml LB, then add 0.1 ml of resuspended colony into the flask containing 500 ml of LB + antibiotic. Grow as described in EXAMPLE IV.

~150,000 U/g. It is about 100 times greater yiueld than from native *Micrococcus* species (NEB#446).

Unfortunately, the MseRM3 strain showed no MseI restriction endonuclease activity after the strain was stored at −70° C. and revived. To solve this problem, the MseI methylase expression level was increased by constructing pVR-26 and pVR-27 plasmids (Example IV above). These strains (MseRM4, MseRM5 and MseRM6) gave high MseI restriction endonuclease yield from even after storing the strain at −70° C. and one strain, MseRM4 (NEB#1284; New England Biolabs, Inc., Beverly, Mass.) was used for scale-up in the 100 L production fermentor (see Example VI). The yield of MseI restriction endonuclease from this larger scale fermentation was $0.5 \times 10^6$ U/g wet cells.

EXAMPLE VI

Production of the Recombinant MseI Restriction Endonuclease

The MseI restriction enzyme was produced form recombinant E. coli strain NEB#1284 propagated to late-log phase in a 100-liter fermenter. A sample of these cells was deposited under the terms and conditions of the Budapest Treaty with the American Type Culture Collection (ATCC), 1801 University Blvd., Manassas, Va. 20110, on Aug. 28, 2000 and received ATCC Accession No. PTA-2421. All restrictions on the availability of the deposited material to the public will be irrevocably removed upon granting of a patent on the present claimed invention.

A) Cell Growth

The transformed *E. coli* host, NEB#1284 containing the recombinant MseI restriction endonuclease clone was stored as a frozen stock solution at −70° C. in 50% glycerol. Cultures used for seed inoculation were streaked onto LB agar plates containing ampicillin (100 µg/ml), chloramphenicol (30 µg/ml) and kanamycin (50 µg/ml) and incubated overnight at 37° C. to obtain single colonies. Several colonies were used to inoculate 10 ml LB medium supplemented with 30 µg of kanamycin/ml 100 µg of ampicillin/ml, and 30 µg of chloramphenicol/ml. Cells were grown for 3 hrs in a shaking incubator at 37° C. and 250 rpm and then at 30° C. for an additional 3.5 hours (to avoid overgrowing the culture). The final corrected Klett of this culture was 122 or mid-log. This culture was used to inoculate 100-liter of LB supplemented with 30 µg of kanamycin/ml 100 µg of ampicillin/ml, and 30 µg of chloramphenicol/ml. The fermentation was run for 18 hours at 30° C. with aeration of 2 SCFM (standard cubic feet per minute) and an agitation rate of 200 rpm. The final corrected Klett was 313. From this fermentation 331 grams of cells (wet weight) were harvested by continuous flow centrifugation and cells were stored at −70° C. A crude extract was made from 1 g of cells and the enzyme activity was estimated, using the method described above (see Example V). The yield of MseI restriction endonuclease in crude extract was 500,000# U/g, which is about 100 times more than in crude extract of *Micrococcus* species (NEB#446).

B) Purification of the MseI Restriction Endonuclease from NEB# 1284

All the following procedures were performed either on ice or at 4° C. 330 grams of cells were suspended in 990 ml Buffer A (0.15 M NaCl, 10 mM Tris pH 7.5, 10 mM BME, 1 mM EDTA and 5% (v/v) glycerol and were broken by 4 passes at psig12K through a Gaulin Press to an O.D. of 0.56. The 1150 ml supernatant was PEG precipitated by adding PEG 6000 to 7.5% and NaCl to 0.5 M and then incubated for 50 minutes at 4° C. The PEG slurry was centrifuged at 12K for 30 minutes at 4° C. The 580 ml of supernatant was diluted to 0.1M NaCl with Buffer A without NaCl and loaded onto a 430 ml Heparin Hyper D column equilibrated with Buffer A. The column was washed with 1200 ml Buffer A and then a 4000 ml linear gradient from 0.1 M NaCl to 1.0 M NaCl was applied. The restriction enzyme activity eluted at 0.25–0.35M NaCl and was pooled. The Heparin Hyper D pool was diluted to 0.1M NaCl with Buffer A without NaCl and loaded onto an 88 ml PEI column equilibrated with buffer A. The column was washed with 100 mls Buffer A and then a 1000 ml linear gradient from 0.1M to 1.7M NaCl was applied. The restriction enzyme activity eluted at 0.7–0.9M NaCl and was dialyzed against Buffer C (50 mM NaCl, 15 mM Tris pH 7.5, 10 mM BME, 0.1 mM EDTA and 5% (v/v) glycerol) overnight and loaded onto a 20 ml Source Q column equilibrated with Buffer C. The column was washed with 40 ml Buffer C and a 400 ml linear gradient from 0.05M NaCl to 1.0M NaCl was applied. The restriction enzyme activity eluted at 0.25M –0.35M NaCl and was pooled. The Source Q pool was dialyzed against Buffer D (10 mM KPO4 pH7.0, 0.075M NaCl, 10 mM BME, 0.1 mM EDTA, 5% (v/v) glycerol) and loaded onto a 20 ml Heparin TSK column equilibrated with Buffer D. The column was washed with 40 ml Buffer D and a 400 ml linear gradient from 0.075 M to 1 M NaCl in buffer D was applied. The restriction enzyme activity eluted at 0.3M –0.4M NaCl and was pooled. BSA was added to a final concentration of 100 µg/ml. The pool was dialyzed to Storage Buffer (20 mM Tris pH 7.5, 0.1M EDTA, 1 mM DTT, 50 mM NaCl, 50% (v/v) glycerol, 200 µg/ml BSA) overnight. This purification scheme yielded 26,000,000 units of MseI restriction endonuclease. The MseI restriction endonuclease obtained from this purification was substantially free of non-specific endonuclease and exonuclease.

The purity of the MseI restriction endonuclease preparation was checked by looking at the following criteria:

1. Ligation: After a 5-fold overdigestion of lambda DNA, greater than 95% of the DNA fragments produced were ligated with T4 DNA Ligase (at a 5' termini concentration of 1–2 µM at 16° C. Of these ligated fragments, 95% were able to be recut.

2. Prolonged digestion: After Incubating a 50 µl reaction containing 1 µg of lambda and 100 units of enzyme for 16 hours, the same banding pattern of DNA bands was produced as a reaction performed in one hour with one unit of enzyme.

3. Exonuclease Activity: After incubation of 100 units of enzyme for 4 hours at 37° C. in a 50 µl reaction containing 1 µg sonicated $^3$H DNA (105 cpm/µg) less than 0.4% radioactivity was released.

All tests were performed in the following reaction buffer: NEBuffer 2 (50 mM NaCl, 10 mM MgCl2, 10 mM Tris-HCl, 1 mM DTT, (pH 7.9 at 25° C., supplemented with 100 µg/ml BSA. Unit determination: Lambda DNA substrate (1.0 µg) was digested in 50 µl 1×MseI reaction buffer (NEBuffer 2) with serial dilutions of MseI endonuclease for 1 hour at 37° C. DNA was fractionated by electrophoresis and visualized by EtdBr staining. Activity was determined by the presence of the appropriate size bands associated with a MseI digestion of lambda DNA. One unit of restriction endonuclease activity is defined as the amount of enzyme required to completely digest 1 µg of substrate DNA in a total reaction volume of 50 µl in one hour using the NEBuffer specified.

What is claimed is:

1. An isolated DNA coding for MseI restriction endonuclease, wherein the isolated DNA is obtainable from ATCC No. PTA-2421.

2. A recombinant DNA vector comprising the isolated DNA of claim 1.

3. An isolated DNA coding for MseI restriction endonuclease and methylase, wherein the isolated DNA is obtainable from ATCC No. PTA-2421.

4. A recombinant DNA vector which comprises the isolated DNA of claim 3.

5. A host cell transformed by the vector of claim 2 or 4.

6. A method of producing the MseI restriction endonmuclease comprising, culturing a host cell transformed with the vector of claim 2 or 4 under conditions suitable for expression of said endonuclease.

* * * * *

UNITED STATES PATENT AND TRADEMARK OFFICE
CERTIFICATE OF CORRECTION

| | | |
|---|---|---|
| PATENT NO. | : 6,846,658 B1 | |
| APPLICATION NO. | : 09/689343 | |
| DATED | : January 25, 2005 | |
| INVENTOR(S) | : Rebecca Kucera et al. | |

It is certified that error appears in the above-identified patent and that said Letters Patent is hereby corrected as shown below:

TITLE PAGE, ITEM (54) TITLE:

Replace "MSEL" with "MseI"

In the Specification:

At column 1, line 2, delete "MSEL" and insert -- MseI --, therefor.

At column 1, line 24, italicize "Ann."

At column 2, line 51, delete "*E. coliL*" and insert -- *E. coli*: --, therefor.

At column 6, line 19, delete "mseI" and insert -- MseI --, therefor.

At column 6, line 21, delete "mseI" and insert -- MseI --, therefor.

At column 7, line 3, delete "6,569,669" and insert -- 6,569,669) --, therefor.

At column 11, line 59, delete "esaDIx5IM" and insert -- esaDix5IM --, therefor.

At column 14, line 16, delete "described – approach" and insert -- described approach --, therefor.

At column 20, line 33, delete "M. MseI" and insert -- M.MseI --, therefor.

At column 20, line 34, delete "pNKR1707 mseIM-9" and insert -- pNKR1707MseIM-9 --, therefor.

At column 20, line 37, delete "EcORI" and insert -- EcoRI --, therefor.

Signed and Sealed this
Twenty-fourth Day of May, 2011

David J. Kappos
*Director of the United States Patent and Trademark Office*

CERTIFICATE OF CORRECTION (continued)
U.S. Pat. No. 6,846,658 B1

At column 20, line 39, delete "Pmel-Af/III" and insert -- Pmel-AflIII --, therefor.

At column 21, line 56, delete "Ac/I" and insert -- AcII --, therefor.

At column 24, lines 37-38, delete "(U.S. application Ser. No. 09/689,359), U.S. Pat. No. 6,569,669" and insert -- (U.S. application Ser. No. 09/689,359, U.S. Pat. No. 6,569,669) --, therefor.

In the Claims:

In Claim 6, Column 48, lines 33-34, delete "endomuclease" and insert -- endonuclease --, therefor.

SEQUENCE LISTING

<160> NUMBER OF SEQ ID NOS: 21

<210> SEQ ID NO 1
<211> LENGTH: 903
<212> TYPE: DNA
<213> ORGANISM: Micrococcus sp.
<220> FEATURE:
<221> NAME/KEY: CDS
<222> LOCATION: (1)..(900)
<223> OTHER INFORMATION:

<400> SEQUENCE: 1

```
atg cct atc tcg acc gtc tgg acg ccg gac gga gac gac ctc atc gtg      48
Met Pro Ile Ser Thr Val Trp Thr Pro Asp Gly Asp Asp Leu Ile Val
1               5                  10                  15 gag gcg gac aac ctc gat ttc att caa acg ctc ccc gac gcg agc ttc      96
Glu Ala Asp Asn Leu Asp Phe Ile Gln Thr Leu Pro Asp Ala Ser Phe
            20                  25                  30 cga atg atc tac atc gat ccg ccg ttc aac aca ggg cga acg cag cgg     144
Arg Met Ile Tyr Ile Asp Pro Pro Phe Asn Thr Gly Arg Thr Gln Arg
        35                  40                  45 ctt cag tcg ctc aag acg acc cgc tcg gtc aca ggg tcg cga gtc ggc     192
Leu Gln Ser Leu Lys Thr Thr Arg Ser Val Thr Gly Ser Arg Val Gly
    50                  55                  60 ttc aaa ggc cag acg tac gac acg gtc aag agc act ctg cac tcg tat     240
Phe Lys Gly Gln Thr Tyr Asp Thr Val Lys Ser Thr Leu His Ser Tyr
65                  70                  75                  80 gac gac gct ttc acc gac tat tgg tcg ttc ctc gaa ccg cgt ctc ctg     288
Asp Asp Ala Phe Thr Asp Tyr Trp Ser Phe Leu Glu Pro Arg Leu Leu
                85                  90                  95 gag gct tgg cgg ttg ctc acc cct gac ggc gcg ctc tat ctt cat ctg     336
Glu Ala Trp Arg Leu Leu Thr Pro Asp Gly Ala Leu Tyr Leu His Leu
            100                 105                 110 gat tac cgc gag gtt cac tac gcc aag gtc gtc ctc gac gcg atg ttc     384
Asp Tyr Arg Glu Val His Tyr Ala Lys Val Val Leu Asp Ala Met Phe
        115                 120                 125 gga cgc gaa agc ttc ctg aac gag ctg atc tgg gcg tac gac tac ggc     432
Gly Arg Glu Ser Phe Leu Asn Glu Leu Ile Trp Ala Tyr Asp Tyr Gly
    130                 135                 140 gcg cgc tcg aag agc aag tgg ccc acc aag cac gac aac atc ctc gtg     480
Ala Arg Ser Lys Ser Lys Trp Pro Thr Lys His Asp Asn Ile Leu Val
145                 150                 155                 160 tat gtg aag gac ccg aac aac tac gtc tgg aac ggt cag gat gta gat     528
Tyr Val Lys Asp Pro Asn Asn Tyr Val Trp Asn Gly Gln Asp Val Asp
                165                 170                 175 cgc gag ccc tac atg gcg ccc ggg ctc gtt aca ccc gag aag gta gcg     576
Arg Glu Pro Tyr Met Ala Pro Gly Leu Val Thr Pro Glu Lys Val Ala
            180                 185                 190 ctt ggc aag ctg ccc acc gac gtc tgg tgg cac aca atc gtt ccg cct     624
Leu Gly Lys Leu Pro Thr Asp Val Trp Trp His Thr Ile Val Pro Pro
        195                 200                 205 gcg agc aaa gag cgc acc ggg tac gcg aca cag aag ccg gtc ggc atc     672
Ala Ser Lys Glu Arg Thr Gly Tyr Ala Thr Gln Lys Pro Val Gly Ile
    210                 215                 220 atc cgt cgc atg att cag gcg agc agc aat gaa ggc gac tgg gtt ctg     720
Ile Arg Arg Met Ile Gln Ala Ser Ser Asn Glu Gly Asp Trp Val Leu
225                 230                 235                 240 gat ttc ttc gct ggt agt ggg acg acc ggc gcc gcg gcc cgc cag ctc     768
Asp Phe Phe Ala Gly Ser Gly Thr Thr Gly Ala Ala Ala Arg Gln Leu
                245                 250                 255
```

```
gga cgc cgt ttt gtg ctc gta gac gtc aac cca gaa gca atc gcg gta    816
Gly Arg Arg Phe Val Leu Val Asp Val Asn Pro Glu Ala Ile Ala Val
        260                 265                 270 atg gca aaa cgg ttg gat gac ggg gca ttg gac acc agc gtg acg atc    864
Met Ala Lys Arg Leu Asp Asp Gly Ala Leu Asp Thr Ser Val Thr Ile
    275                 280                 285 gtg cag act ccc cag agt gac cca cga acc gac gga tga                903
Val Gln Thr Pro Gln Ser Asp Pro Arg Thr Asp Gly
290                 295                 300
```

<210> SEQ ID NO 2
<211> LENGTH: 300
<212> TYPE: PRT
<213> ORGANISM: Micrococcus sp.

<400> SEQUENCE: 2

```
Met Pro Ile Ser Thr Val Trp Thr Pro Asp Gly Asp Leu Ile Val
1               5                   10                  15

Glu Ala Asp Asn Leu Asp Phe Ile Gln Thr Leu Pro Asp Ala Ser Phe
                20                  25                  30

Arg Met Ile Tyr Ile Asp Pro Pro Phe Asn Thr Gly Arg Thr Gln Arg
            35                  40                  45

Leu Gln Ser Leu Lys Thr Thr Arg Ser Val Thr Gly Ser Arg Val Gly
        50                  55                  60

Phe Lys Gly Gln Thr Tyr Asp Thr Val Lys Ser Thr Leu His Ser Tyr
65                  70                  75                  80

Asp Asp Ala Phe Thr Asp Tyr Trp Ser Phe Leu Glu Pro Arg Leu Leu
                85                  90                  95

Glu Ala Trp Arg Leu Leu Thr Pro Asp Gly Ala Leu Tyr Leu His Leu
            100                 105                 110

Asp Tyr Arg Glu Val His Tyr Ala Lys Val Val Leu Asp Ala Met Phe
        115                 120                 125

Gly Arg Glu Ser Phe Leu Asn Glu Leu Ile Trp Ala Tyr Asp Tyr Gly
    130                 135                 140

Ala Arg Ser Lys Ser Lys Trp Pro Thr Lys His Asp Asn Ile Leu Val
145                 150                 155                 160

Tyr Val Lys Asp Pro Asn Asn Tyr Val Trp Asn Gly Gln Asp Val Asp
                165                 170                 175

Arg Glu Pro Tyr Met Ala Pro Gly Leu Val Thr Pro Glu Lys Val Ala
            180                 185                 190

Leu Gly Lys Leu Pro Thr Asp Val Trp Trp His Thr Ile Val Pro Pro
        195                 200                 205

Ala Ser Lys Glu Arg Thr Gly Tyr Ala Thr Gln Lys Pro Val Gly Ile
    210                 215                 220

Ile Arg Arg Met Ile Gln Ala Ser Ser Asn Glu Gly Asp Trp Val Leu
225                 230                 235                 240

Asp Phe Phe Ala Gly Ser Gly Thr Thr Gly Ala Ala Ala Arg Gln Leu
                245                 250                 255

Gly Arg Arg Phe Val Leu Val Asp Val Asn Pro Glu Ala Ile Ala Val
            260                 265                 270

Met Ala Lys Arg Leu Asp Asp Gly Ala Leu Asp Thr Ser Val Thr Ile
        275                 280                 285

Val Gln Thr Pro Gln Ser Asp Pro Arg Thr Asp Gly
    290                 295                 300
```

-continued

```
<210> SEQ ID NO 3
<211> LENGTH: 1236
<212> TYPE: DNA
<213> ORGANISM: Unknown
<220> FEATURE:
<223> OTHER INFORMATION: Environmental DNA
<220> FEATURE:
<221> NAME/KEY: CDS
<222> LOCATION: (1)..(1233)
<223> OTHER INFORMATION:
<220> FEATURE:
<221> NAME/KEY: misc_feature
<222> LOCATION: (198)..(198)
<223> OTHER INFORMATION: Xaa = any amino acid
<220> FEATURE:
<221> NAME/KEY: misc_feature
<222> LOCATION: (594)..(594)
<223> OTHER INFORMATION: N= G, A, C or T

<400> SEQUENCE: 3 atg cct aca ctg gat tgg ccc ggt aaa cag tta agc ttc cca cca gct     48
Met Pro Thr Leu Asp Trp Pro Gly Lys Gln Leu Ser Phe Pro Pro Ala
 1               5                  10                  15 acc tcc ttg cat ctg gag agt gtg gtc act gag gga gcg gag tca ccg     96
Thr Ser Leu His Leu Glu Ser Val Val Thr Glu Gly Ala Glu Ser Pro
             20                  25                  30 cct aat cgt ctg att tgg gcg gac aac ctg ccg cta atg gta gat ttg    144
Pro Asn Arg Leu Ile Trp Ala Asp Asn Leu Pro Leu Met Val Asp Leu
         35                  40                  45 ttg gcc gaa tat gaa ggg aaa atc gat ctg atc tac gcc gat ccc cct    192
Leu Ala Glu Tyr Glu Gly Lys Ile Asp Leu Ile Tyr Ala Asp Pro Pro
     50                  55                  60 ttt ttt acg gat cgt act tat gcg gcg cga att ggt cat ggg gag gat    240
Phe Phe Thr Asp Arg Thr Tyr Ala Ala Arg Ile Gly His Gly Glu Asp
 65                  70                  75                  80 tcg cgt cgt cca caa acc tgg cag ctt gca gaa gga tat acg gac gag    288
Ser Arg Arg Pro Gln Thr Trp Gln Leu Ala Glu Gly Tyr Thr Asp Glu
                 85                  90                  95 tgg aag gat tta gat gaa tac ctg gac ttc ctt tat cca cgc ctg gta    336
Trp Lys Asp Leu Asp Glu Tyr Leu Asp Phe Leu Tyr Pro Arg Leu Val
            100                 105                 110 ctg atg tat cga ctg ctg gca cca cac gga acg ctc tac ttg cac ctg    384
Leu Met Tyr Arg Leu Leu Ala Pro His Gly Thr Leu Tyr Leu His Leu
        115                 120                 125 gac tgg cac gcc aat gcc tac gta cgt gta ctg ctt gat gag atc ttc    432
Asp Trp His Ala Asn Ala Tyr Val Arg Val Leu Leu Asp Glu Ile Phe
    130                 135                 140 ggg cga cag cgg ttt ctc aac gag atc gtc tgg atc tat cac ggc ccc    480
Gly Arg Gln Arg Phe Leu Asn Glu Ile Val Trp Ile Tyr His Gly Pro
145                 150                 155                 160 tca gcc atc cga cgc gcc ttc aag cgc aaa cat gat acc atc ttg gtt    528
Ser Ala Ile Arg Arg Ala Phe Lys Arg Lys His Asp Thr Ile Leu Val
                165                 170                 175 tat gtg aaa ggt gaa aac tat aca ttc aat gcg gat gcg gtt cgt caa    576
Tyr Val Lys Gly Glu Asn Tyr Thr Phe Asn Ala Asp Ala Val Arg Gln
            180                 185                 190 cct tac cat ccg agc acn cat aag acc ttc gct tcc tcc ccg aag gcc    624
Pro Tyr His Pro Ser Xaa His Lys Thr Phe Ala Ser Ser Pro Lys Ala
        195                 200                 205 ggc ttt ggt aag gtg ccg gat ctg cag cgc ggc aaa gtg ccc gaa gac    672
Gly Phe Gly Lys Val Pro Asp Leu Gln Arg Gly Lys Val Pro Glu Asp
    210                 215                 220 tgg tgg tat ttt ccg gtc gtg gcc cgt cta cac cga gaa cgg agc ggc    720
Trp Trp Tyr Phe Pro Val Val Ala Arg Leu His Arg Glu Arg Ser Gly
225                 230                 235                 240
```

-continued

| | | | |
|---|---|---|---|
| tat ccg act caa aag cct caa gcc ttg ctg gag cgg atc ctg ctg gcc<br>Tyr Pro Thr Gln Lys Pro Gln Ala Leu Leu Glu Arg Ile Leu Leu Ala<br>  225                           230                        235                        240 | 768 |

```
tat ccg act caa aag cct caa gcc ttg ctg gag cgg atc ctg ctg gcc      768
Tyr Pro Thr Gln Lys Pro Gln Ala Leu Leu Glu Arg Ile Leu Leu Ala
            245                 250                 255 tcc tcg aac gca ggc gat ctg gtg gca gac ttc ttc tgc ggc tca ggg      816
Ser Ser Asn Ala Gly Asp Leu Val Ala Asp Phe Phe Cys Gly Ser Gly
                260                 265                 270 aca acc gct gtg gtg gca gcc cgt ctg gga cgg cgc ttc ctg gtc aac      864
Thr Thr Ala Val Val Ala Ala Arg Leu Gly Arg Arg Phe Leu Val Asn
        275                 280                 285 gat gca agc tgg cgc gcc gtt cat gtg aca cgc aca cgc ttg cta cgc      912
Asp Ala Ser Trp Arg Ala Val His Val Thr Arg Thr Arg Leu Leu Arg
    290                 295                 300 gag gga gta agt ttc act ttt gaa cgc cag gaa act ttt act cta cct      960
Glu Gly Val Ser Phe Thr Phe Glu Arg Gln Glu Thr Phe Thr Leu Pro
305                 310                 315                 320 atc cag cca ctt cca cca gat tgg ttg atc atc gcc gag gag cag att     1008
Ile Gln Pro Leu Pro Pro Asp Trp Leu Ile Ile Ala Glu Glu Gln Ile
                325                 330                 335 cgc ctc caa gca ccc ttt ctc gta gat ttt tgg gaa gtg gac gat caa     1056
Arg Leu Gln Ala Pro Phe Leu Val Asp Phe Trp Glu Val Asp Asp Gln
            340                 345                 350 tgg gat ggc aaa atc ttc cgc agc cgt cat caa ggc tta cgc tcc cgc     1104
Trp Asp Gly Lys Ile Phe Arg Ser Arg His Gln Gly Leu Arg Ser Arg
        355                 360                 365 ctt cag gag cag gcg ccg ctc tct cta cca ttg acc ggg aat gga ctg     1152
Leu Gln Glu Gln Ala Pro Leu Ser Leu Pro Leu Thr Gly Asn Gly Leu
    370                 375                 380 ttg tgt gta cgg gta gtg agc cgt gaa ggg gaa tac tat gag ttc aca     1200
Leu Cys Val Arg Val Val Ser Arg Glu Gly Glu Tyr Tyr Glu Phe Thr
385                 390                 395                 400 ggt cga gcc gat agc cct cac ccc gta tcg ttt tga                     1236
Gly Arg Ala Asp Ser Pro His Pro Val Ser Phe
                405                 410
```

<210> SEQ ID NO 4
<211> LENGTH: 411
<212> TYPE: PRT
<213> ORGANISM: Unknown
<220> FEATURE:
<223> OTHER INFORMATION: Environmental DNA
<220> FEATURE:
<221> NAME/KEY: misc_feature
<222> LOCATION: (198)..(198)
<223> OTHER INFORMATION: Xaa = any amino acid

<400> SEQUENCE: 4

```
Met Pro Thr Leu Asp Trp Pro Gly Lys Gln Leu Ser Phe Pro Pro Ala
  1               5                  10                  15

Thr Ser Leu His Leu Glu Ser Val Val Thr Glu Gly Ala Glu Ser Pro
             20                  25                  30

Pro Asn Arg Leu Ile Trp Ala Asp Asn Leu Pro Leu Met Val Asp Leu
         35                  40                  45

Leu Ala Glu Tyr Glu Gly Lys Ile Asp Leu Ile Tyr Ala Asp Pro Pro
     50                  55                  60

Phe Phe Thr Asp Arg Thr Tyr Ala Ala Arg Ile Gly His Gly Glu Asp
 65                  70                  75                  80

Ser Arg Arg Pro Gln Thr Trp Gln Leu Ala Glu Gly Tyr Thr Asp Glu
                 85                  90                  95

Trp Lys Asp Leu Asp Glu Tyr Leu Asp Phe Leu Tyr Pro Arg Leu Val
```

```
                      100                 105                 110
Leu Met Tyr Arg Leu Leu Ala Pro His Gly Thr Leu Tyr Leu His Leu
        115                 120                 125

Asp Trp His Ala Asn Ala Tyr Val Arg Val Leu Leu Asp Glu Ile Phe
130                 135                 140

Gly Arg Gln Arg Phe Leu Asn Glu Ile Val Trp Ile Tyr His Gly Pro
145                 150                 155                 160

Ser Ala Ile Arg Arg Ala Phe Lys Arg Lys His Asp Thr Ile Leu Val
                165                 170                 175

Tyr Val Lys Gly Glu Asn Tyr Thr Phe Asn Ala Asp Ala Val Arg Gln
            180                 185                 190

Pro Tyr His Pro Ser Xaa His Lys Thr Phe Ala Ser Ser Pro Lys Ala
        195                 200                 205

Gly Phe Gly Lys Val Pro Asp Leu Gln Arg Gly Lys Val Pro Glu Asp
    210                 215                 220

Trp Trp Tyr Phe Pro Val Val Ala Arg Leu His Arg Glu Arg Ser Gly
225                 230                 235                 240

Tyr Pro Thr Gln Lys Pro Gln Ala Leu Leu Glu Arg Ile Leu Leu Ala
                245                 250                 255

Ser Ser Asn Ala Gly Asp Leu Val Ala Asp Phe Phe Cys Gly Ser Gly
            260                 265                 270

Thr Thr Ala Val Val Ala Ala Arg Leu Gly Arg Arg Phe Leu Val Asn
        275                 280                 285

Asp Ala Ser Trp Arg Ala Val His Val Thr Arg Thr Arg Leu Leu Arg
    290                 295                 300

Glu Gly Val Ser Phe Thr Phe Glu Arg Gln Glu Thr Phe Thr Leu Pro
305                 310                 315                 320

Ile Gln Pro Leu Pro Pro Asp Trp Leu Ile Ile Ala Glu Glu Gln Ile
                325                 330                 335

Arg Leu Gln Ala Pro Phe Leu Val Asp Phe Trp Glu Val Asp Asp Gln
            340                 345                 350

Trp Asp Gly Lys Ile Phe Arg Ser Arg His Gln Gly Leu Arg Ser Arg
        355                 360                 365

Leu Gln Glu Gln Ala Pro Leu Ser Leu Pro Leu Thr Gly Asn Gly Leu
    370                 375                 380

Leu Cys Val Arg Val Val Ser Arg Glu Gly Glu Tyr Tyr Glu Phe Thr
385                 390                 395                 400

Gly Arg Ala Asp Ser Pro His Pro Val Ser Phe
                405                 410

<210> SEQ ID NO 5
<211> LENGTH: 924
<212> TYPE: DNA
<213> ORGANISM: Unknown
<220> FEATURE:
<223> OTHER INFORMATION: Environmental DNA
<220> FEATURE:
<221> NAME/KEY: CDS
<222> LOCATION: (1)..(921)
<223> OTHER INFORMATION:

<400> SEQUENCE: 5 atg atc acg aac ctg atg gaa aac gat gtc att ggc aaa atc tac ttt    48
Met Ile Thr Asn Leu Met Glu Asn Asp Val Ile Gly Lys Ile Tyr Phe
1               5                  10                  15 gcc gac aac atg gaa gtc ctg cga ggg ctt ccg gcg gcg tcc gtg gac    96
Ala Asp Asn Met Glu Val Leu Arg Gly Leu Pro Ala Ala Ser Val Asp
```

```
            20                  25                  30
ctg atc tac atc gat cct ccg ttc aac acc gga aag gtt cag gag cgc      144
Leu Ile Tyr Ile Asp Pro Pro Phe Asn Thr Gly Lys Val Gln Glu Arg
             35                  40                  45 act cag ctc aaa acg gtg cgc tcc gag tgg ggc gat cgc gtc gga ttc      192
Thr Gln Leu Lys Thr Val Arg Ser Glu Trp Gly Asp Arg Val Gly Phe
 50                  55                  60 cag ggc cgt cgc tac gaa agc atc gtc gtg ggt aag aag cgc ttt acc      240
Gln Gly Arg Arg Tyr Glu Ser Ile Val Val Gly Lys Lys Arg Phe Thr
 65                  70                  75                  80 gac ttc ttc gac gac tat ctg gct ttc ctg gaa ccg cgc ctg gtc gaa      288
Asp Phe Phe Asp Asp Tyr Leu Ala Phe Leu Glu Pro Arg Leu Val Glu
                 85                  90                  95 gcc cat cgt gtt ctg gcg ccg cac ggg tgc ctc tac ttt cac gtc gac      336
Ala His Arg Val Leu Ala Pro His Gly Cys Leu Tyr Phe His Val Asp
            100                 105                 110 tac cgc gag gtg cac tac tgt aag gtc ctt ctt gac ggc atc ttc ggt      384
Tyr Arg Glu Val His Tyr Cys Lys Val Leu Leu Asp Gly Ile Phe Gly
        115                 120                 125 cgc gag gcc ttt ctc aac gag atc atc tgg gcc tac gat tac ggc ggg      432
Arg Glu Ala Phe Leu Asn Glu Ile Ile Trp Ala Tyr Asp Tyr Gly Gly
    130                 135                 140 cgt ccg aag gac agg tgg cct cct aag cac gac aac atc ctg ctc tac      480
Arg Pro Lys Asp Arg Trp Pro Pro Lys His Asp Asn Ile Leu Leu Tyr
145                 150                 155                 160 gcc aag act ccc ggt cgc cac gtg ttc aat gcg gac gaa atc gag cgc      528
Ala Lys Thr Pro Gly Arg His Val Phe Asn Ala Asp Glu Ile Glu Arg
                165                 170                 175 att ccc tac atg gct ccg ggc ctg gtt ggc ccc gaa aag gca gcc cgt      576
Ile Pro Tyr Met Ala Pro Gly Leu Val Gly Pro Glu Lys Ala Ala Arg
            180                 185                 190 gga aaa ctg cca acc gac acg tgg tgg cat acg atc gtt ccg acc agc      624
Gly Lys Leu Pro Thr Asp Thr Trp Trp His Thr Ile Val Pro Thr Ser
        195                 200                 205 ggc tcc gag aag acc ggg tat cca acc cag aaa cct tta ggg att ctc      672
Gly Ser Glu Lys Thr Gly Tyr Pro Thr Gln Lys Pro Leu Gly Ile Leu
    210                 215                 220 cgc cgt att gtg cag gca tcg tct cat ccg ggg gca gtc gtg ctc gac      720
Arg Arg Ile Val Gln Ala Ser Ser His Pro Gly Ala Val Val Leu Asp
225                 230                 235                 240 ttc ttc gcc ggc agt ggg aca aca ggg gta gcg gct ttt gag ttg ggc      768
Phe Phe Ala Gly Ser Gly Thr Thr Gly Val Ala Ala Phe Glu Leu Gly
                245                 250                 255 cgg cgt ttc att ctg gtc gat aac cat ccg gag gcc ctc cag gtg atg      816
Arg Arg Phe Ile Leu Val Asp Asn His Pro Glu Ala Leu Gln Val Met
            260                 265                 270 gcc agg cgc ttc gac ggc atc gag ggg atc gaa tgg gtg ggc ttc gat      864
Ala Arg Arg Phe Asp Gly Ile Glu Gly Ile Glu Trp Val Gly Phe Asp
        275                 280                 285 ccg aca ccg tac cag aag ggc gca aag cag cgc cgc tcc tgc ccg gcg      912
Pro Thr Pro Tyr Gln Lys Gly Ala Lys Gln Arg Arg Ser Cys Pro Ala
    290                 295                 300 ccc acc ggg taa                                                      924
Pro Thr Gly
305
```

<210> SEQ ID NO 6
<211> LENGTH: 307
<212> TYPE: PRT
<213> ORGANISM: Unknown

```
<220> FEATURE:
<223> OTHER INFORMATION: Environmental DNA

<400> SEQUENCE: 6

Met Ile Thr Asn Leu Met Glu Asn Asp Val Ile Gly Lys Ile Tyr Phe
1               5                   10                  15

Ala Asp Asn Met Glu Val Leu Arg Gly Leu Pro Ala Ala Ser Val Asp
            20                  25                  30

Leu Ile Tyr Ile Asp Pro Pro Phe Asn Thr Gly Lys Val Gln Glu Arg
        35                  40                  45

Thr Gln Leu Lys Thr Val Arg Ser Glu Trp Gly Asp Arg Val Gly Phe
    50                  55                  60

Gln Gly Arg Arg Tyr Glu Ser Ile Val Gly Lys Lys Arg Phe Thr
65                  70                  75                  80

Asp Phe Phe Asp Asp Tyr Leu Ala Phe Leu Glu Pro Arg Leu Val Glu
                85                  90                  95

Ala His Arg Val Leu Ala Pro His Gly Cys Leu Tyr Phe His Val Asp
            100                 105                 110

Tyr Arg Glu Val His Tyr Cys Lys Val Leu Leu Asp Gly Ile Phe Gly
        115                 120                 125

Arg Glu Ala Phe Leu Asn Glu Ile Ile Trp Ala Tyr Asp Tyr Gly Gly
    130                 135                 140

Arg Pro Lys Asp Arg Trp Pro Pro Lys His Asp Asn Ile Leu Leu Tyr
145                 150                 155                 160

Ala Lys Thr Pro Gly Arg His Val Phe Asn Ala Asp Glu Ile Glu Arg
                165                 170                 175

Ile Pro Tyr Met Ala Pro Gly Leu Val Gly Pro Glu Lys Ala Ala Arg
            180                 185                 190

Gly Lys Leu Pro Thr Asp Thr Trp His Thr Ile Val Pro Thr Ser
        195                 200                 205

Gly Ser Glu Lys Thr Gly Tyr Pro Thr Gln Lys Pro Leu Gly Ile Leu
    210                 215                 220

Arg Arg Ile Val Gln Ala Ser Ser His Pro Gly Ala Val Val Leu Asp
225                 230                 235                 240

Phe Phe Ala Gly Ser Gly Thr Thr Gly Val Ala Ala Phe Glu Leu Gly
                245                 250                 255

Arg Arg Phe Ile Leu Val Asp Asn His Pro Glu Ala Leu Gln Val Met
            260                 265                 270

Ala Arg Arg Phe Asp Gly Ile Glu Gly Ile Glu Trp Val Gly Phe Asp
        275                 280                 285

Pro Thr Pro Tyr Gln Lys Gly Ala Lys Gln Arg Arg Ser Cys Pro Ala
    290                 295                 300

Pro Thr Gly
305

<210> SEQ ID NO 7
<211> LENGTH: 561
<212> TYPE: DNA
<213> ORGANISM: Micrococcus sp.
<220> FEATURE:
<221> NAME/KEY: CDS
<222> LOCATION: (1)..(558)
<223> OTHER INFORMATION:

<400> SEQUENCE: 7 gtg acc cac gaa ccg acg gat gat ccc gat ttc ata gtg atg gcc gcg     48
Val Thr His Glu Pro Thr Asp Asp Pro Asp Phe Ile Val Met Ala Ala
```

```
           1               5                  10                 15
agc gcg gcg aac ctc gct gat cgg tac gta gcg agt gaa gac gac ccc     96
Ser Ala Ala Asn Leu Ala Asp Arg Tyr Val Ala Ser Glu Asp Asp Pro
                 20                  25                 30 tgg gtc ggc agc ccg ttc gag tgg atc ctt cgc gtt cca tcc aga acg    144
Trp Val Gly Ser Pro Phe Glu Trp Ile Leu Arg Val Pro Ser Arg Thr
         35                  40                 45 aag ggc gcg gtc ggt gag ctg ctc gtg agc gaa tgg gct aat gcc aaa    192
Lys Gly Ala Val Gly Glu Leu Leu Val Ser Glu Trp Ala Asn Ala Lys
 50                  55                  60 ggc ctc cgt gtg aag agg tcg ggg tcc agc gat gcg gac cgt gtg atc    240
Gly Leu Arg Val Lys Arg Ser Gly Ser Ser Asp Ala Asp Arg Val Ile
 65                  70                  75                  80 aac ggg cat cgc atc gag atc aag atg tcg act ttg tgg aag tcc ggc    288
Asn Gly His Arg Ile Glu Ile Lys Met Ser Thr Leu Trp Lys Ser Gly
                 85                  90                  95 ggc ttc aag ttt cag cag atc cgg gat cag gag tac gac ttt tgc ctc    336
Gly Phe Lys Phe Gln Gln Ile Arg Asp Gln Glu Tyr Asp Phe Cys Leu
         100                 105                110 tgc ctt ggg atc agc ccg ttc gaa gtg cac gcg tgg ctg ctg ccc aaa    384
Cys Leu Gly Ile Ser Pro Phe Glu Val His Ala Trp Leu Leu Pro Lys
         115                 120                125 gac cta ttg ctt gag tac gtg att ggt cac atg ggt cag cac acc ggc    432
Asp Leu Leu Leu Glu Tyr Val Ile Gly His Met Gly Gln His Thr Gly
130                 135                 140 gcg agc ggg agc gac act gcg tgg ctg ggg ttc cca gcg gac gag ccg    480
Ala Ser Gly Ser Asp Thr Ala Trp Leu Gly Phe Pro Ala Asp Glu Pro
145                 150                 155                 160 tat gac tgg atg cgc cct ttc gga ggt cgc tta ggt cac gtc gaa gat    528
Tyr Asp Trp Met Arg Pro Phe Gly Gly Arg Leu Gly His Val Glu Asp
                 165                 170                 175 ctc ctc ctc gcg gcc ggc ccc ggt ccc tac tga                        561
Leu Leu Leu Ala Ala Gly Pro Gly Pro Tyr
                 180                 185

<210> SEQ ID NO 8
<211> LENGTH: 186
<212> TYPE: PRT
<213> ORGANISM: Micrococcus sp.

<400> SEQUENCE: 8

Val Thr His Glu Pro Thr Asp Pro Asp Phe Ile Val Met Ala Ala
 1               5                  10                  15

Ser Ala Ala Asn Leu Ala Asp Arg Tyr Val Ala Ser Glu Asp Asp Pro
                 20                  25                  30

Trp Val Gly Ser Pro Phe Glu Trp Ile Leu Arg Val Pro Ser Arg Thr
         35                  40                  45

Lys Gly Ala Val Gly Glu Leu Leu Val Ser Glu Trp Ala Asn Ala Lys
 50                  55                  60

Gly Leu Arg Val Lys Arg Ser Gly Ser Ser Asp Ala Asp Arg Val Ile
 65                  70                  75                  80

Asn Gly His Arg Ile Glu Ile Lys Met Ser Thr Leu Trp Lys Ser Gly
                 85                  90                  95

Gly Phe Lys Phe Gln Gln Ile Arg Asp Gln Glu Tyr Asp Phe Cys Leu
         100                 105                 110

Cys Leu Gly Ile Ser Pro Phe Glu Val His Ala Trp Leu Leu Pro Lys
         115                 120                 125

Asp Leu Leu Leu Glu Tyr Val Ile Gly His Met Gly Gln His Thr Gly
```

```
                130                 135                 140
Ala Ser Gly Ser Asp Thr Ala Trp Leu Gly Phe Pro Ala Asp Glu Pro
145                 150                 155                 160

Tyr Asp Trp Met Arg Pro Phe Gly Gly Arg Leu Gly His Val Glu Asp
                165                 170                 175

Leu Leu Leu Ala Ala Gly Pro Gly Pro Tyr
            180                 185

<210> SEQ ID NO 9
<211> LENGTH: 413
<212> TYPE: DNA
<213> ORGANISM: Escherichia coli

<400> SEQUENCE: 9
accggtgatt ggacattgcc gaaatcaggc tgtctctcac tatttgacgc actggctgga      60
ctatccacat ctaccttatt cccccgaata acgagatccc ttccagcacc gggcaattgc     120
ccggtttttt ttgcgttgaa tttgtcattt tgtgccgtgg tgtttaaacc gcacagaata     180
aattgtcgtg atttcacctt taaaataaaa ttaaaagaga aaaaaattct ctgtggaagg     240
gctatgttag ataaaattga ccgtaagctg ctggccttac tgcagcagga ttgcacccte     300 tctttgcagg cactggctga agccgttaat ctgacaacca ccccttgctg gaagcgcctg     360
aaacggctgg aggacgacgg tatccttatc ggcaaagtcg ccctgctgga tcc           413

<210> SEQ ID NO 10
<211> LENGTH: 25
<212> TYPE: PRT
<213> ORGANISM: Micrococcus sp.
<220> FEATURE:
<221> NAME/KEY: MISC_FEATURE
<222> LOCATION: (19)..(19)
<223> OTHER INFORMATION: Xaa = any amino acid
<220> FEATURE:
<221> NAME/KEY: MISC_FEATURE
<222> LOCATION: (24)..(24)
<223> OTHER INFORMATION: Xaa = any amino acid

<400> SEQUENCE: 10

Met Thr His Glu Pro Thr Asp Asp Pro Asp Phe Ile Val Met Ala Ala
1               5                   10                  15

Ser Ala Xaa Asn Leu Ala Asp Xaa Tyr
            20                  25

<210> SEQ ID NO 11
<211> LENGTH: 28
<212> TYPE: DNA
<213> ORGANISM: unknown
<220> FEATURE:
<223> OTHER INFORMATION: Primer MseI-IP1

<400> SEQUENCE: 11
cttctgcagc cgatttcata gtgatggc                                         28

<210> SEQ ID NO 12
<211> LENGTH: 27
<212> TYPE: DNA
<213> ORGANISM: Unknown
<220> FEATURE:
<223> OTHER INFORMATION: Primer MseI-IP2

<400> SEQUENCE: 12
gttctgcaga tcgggatcat ccgtcgg                                          27
```

<210> SEQ ID NO 13
<211> LENGTH: 49
<212> TYPE: DNA
<213> ORGANISM: unknown
<220> FEATURE:
<223> OTHER INFORMATION: Primer MseI-IP3

<400> SEQUENCE: 13
ggttctgcag ttaaggaggt ttaacatatg acccacgaac cgacggatg         49

<210> SEQ ID NO 14
<211> LENGTH: 35
<212> TYPE: DNA
<213> ORGANISM: unknown
<220> FEATURE:
<223> OTHER INFORMATION: Primer MseI-IP4

<400> SEQUENCE: 14
gttggatccg tcgacgcttc tcggcgtacc gagcg                        35

<210> SEQ ID NO 15
<211> LENGTH: 32
<212> TYPE: DNA
<213> ORGANISM: unknown
<220> FEATURE:
<223> OTHER INFORMATION: Primer

<400> SEQUENCE: 15
gaaccggatc cgaccctgag tgagaacatg cc                           32

<210> SEQ ID NO 16
<211> LENGTH: 36
<212> TYPE: DNA
<213> ORGANISM: Unknown
<220> FEATURE:
<223> OTHER INFORMATION: primer

<400> SEQUENCE: 16
aggtcgcaat tgccaggggt cgtcttcact cgctac                       36

<210> SEQ ID NO 17
<211> LENGTH: 30
<212> TYPE: DNA
<213> ORGANISM: unknown
<220> FEATURE:
<223> OTHER INFORMATION: primer

<400> SEQUENCE: 17
gcgatacaga ccggttcaga caggataaag                              30

<210> SEQ ID NO 18
<211> LENGTH: 24
<212> TYPE: DNA
<213> ORGANISM: unknown
<220> FEATURE:
<223> OTHER INFORMATION: primer

<400> SEQUENCE: 18
ggtcggatcc ggcgatacag cgag                                    24

<210> SEQ ID NO 19
<211> LENGTH: 24
<212> TYPE: DNA
<213> ORGANISM: unknown
<220> FEATURE:
<223> OTHER INFORMATION: primer

```
<400> SEQUENCE: 19
ggatcttcca gtggtgcatg aacg                                          24

<210> SEQ ID NO 20
<211> LENGTH: 34
<212> TYPE: DNA
<213> ORGANISM: unknown
<220> FEATURE:
<223> OTHER INFORMATION: forward primer

<400> SEQUENCE: 20
agactccccc atatgaccca cgaaccgacg gatg                               34

<210> SEQ ID NO 21
<211> LENGTH: 34
<212> TYPE: DNA
<213> ORGANISM: unknown
<220> FEATURE:
<223> OTHER INFORMATION: reverse primer

<400> SEQUENCE: 21
gggtggtccc gctagctatt agtagggacc gggg                               34
```